(12) United States Patent
O'Brien et al.

(10) Patent No.: US 12,220,306 B2
(45) Date of Patent: Feb. 11, 2025

(54) METHODS AND APPARATUS FOR TREATMENT OF ANEURYSMS ADJACENT BRANCH ARTERIES

(71) Applicant: Medtronic Vascular, Inc., Santa Rosa, CA (US)

(72) Inventors: Prema Ganesan O'Brien, San Francisco, CA (US); Jonathan Morris, Keller, TX (US); David Erickson, Memphis, TN (US); Matthew Rust, Santa Rosa, CA (US); Curtis Hanson, San Diego, CA (US); Jack Chu, Santa Rosa, CA (US); Charles Thomas, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 197 days.

(21) Appl. No.: 17/960,913

(22) Filed: Oct. 6, 2022

(65) Prior Publication Data
US 2023/0041321 A1 Feb. 9, 2023

Related U.S. Application Data

(63) Continuation of application No. 16/426,610, filed on May 30, 2019, now Pat. No. 11,504,223, which is a continuation of application No. 13/091,363, filed on Apr. 21, 2011, now Pat. No. 10,307,244, which is a continuation of application No. 11/117,978, filed on Apr. 29, 2005, now abandoned.

(51) Int. Cl.
*A61F 2/07* (2013.01)
*A61F 2/06* (2013.01)
*A61F 2/89* (2013.01)
*A61F 2/90* (2013.01)

(52) U.S. Cl.
CPC .......... *A61F 2/07* (2013.01); *A61F 2002/061* (2013.01); *A61F 2002/075* (2013.01); *A61F 2/89* (2013.01); *A61F 2/90* (2013.01); *A61F 2220/005* (2013.01); *A61F 2220/0075* (2013.01)

(58) Field of Classification Search
CPC ......... A61F 2/07; A61F 2002/061; A61F 2/06
See application file for complete search history.

(56) References Cited

U.S. PATENT DOCUMENTS

| | | |
|---|---|---|
| 5,683,451 A | 11/1997 | Lenker et al. |
| 5,713,917 A | 2/1998 | Leonhardt et al. |
| 5,824,040 A | 10/1998 | Cox et al. |
| 5,855,598 A | 1/1999 | Pinchuk et al. |
| 5,906,641 A | 5/1999 | Thompson et al. |
| 5,984,955 A | 11/1999 | Wisselink et al. |
| 6,059,834 A | 5/2000 | Springs |
| 6,093,203 A | 7/2000 | Uflacker et al. |
| 6,129,756 A | 10/2000 | Kugler et al. |
| 6,428,565 B1 | 8/2002 | Wisselink |
| 6,579,312 B2 | 6/2003 | Wilson et al. |
| 6,585,756 B1 | 7/2003 | Strecker |

(Continued)

FOREIGN PATENT DOCUMENTS

EP 1386624 A1 2/2004

*Primary Examiner* — Ashley L Fishback
(74) *Attorney, Agent, or Firm* — Medler Ferro Woodhouse & Mills PLLC

(57) ABSTRACT

A polymer coating/ring is employed to aid in the sealing and connection of modular elements used in body flow lumens for the exclusion and bypass of diseased regions of the flow lumen, such as where aneurysm occurs adjacent to branching blood vessels.

17 Claims, 15 Drawing Sheets

(56) References Cited

U.S. PATENT DOCUMENTS

| | | |
|---|---|---|
| 6,645,242 B1 | 11/2003 | Quinn |
| 6,652,571 B1 | 11/2003 | White et al. |
| 6,656,214 B1 | 12/2003 | Fogarty et al. |
| 2001/0003161 A1 | 6/2001 | Vardi et al. |
| 2001/0006640 A1 | 7/2001 | Grainger |
| 2002/0198585 A1 | 12/2002 | Wisselink |
| 2003/0130720 A1 | 7/2003 | Depalma et al. |
| 2004/0117003 A1 | 6/2004 | Ouriel et al. |
| 2005/0131518 A1 | 6/2005 | Hartley |
| 2005/0137677 A1 | 6/2005 | Rush |
| 2006/0155359 A1 | 7/2006 | Watson |
| 2006/0155366 A1 | 7/2006 | Laduca et al. |

METHODS AND APPARATUS FOR TREATMENT OF ANEURYSMS ADJACENT BRANCH ARTERIES

RELATED APPLICATIONS

This application is a continuation of U.S. patent application Ser. No. 16/426,610, filed May 30, 2019, which is a continuation of U.S. patent application Ser. No. 13/091,363, filed Apr. 21, 2011, now U.S. Pat. No. 10,307,244, which is a continuation of U.S. patent application Ser. No. 11/117,978, filed Apr. 29, 2005, now abandoned, the disclosures of each of which are incorporated by reference herein in their entirety.

FIELD OF THE INVENTION

The field of the invention is the treatment of vascular abnormalities. More particularly, the field of the invention is the treatment of vascular abnormalities by placing an excluding device in a blood vessel to exclude or bypass an abnormality, including placing such an excluding device in an area near one or more branch vessels so as to bypass the abnormality, but not occlude the branch vessel.

BACKGROUND OF THE INVENTION

"Aortic aneurysm" is the term used to describe a condition where a segment of the aorta is dilated to a diameter greater than its original diameter. Aneurysms can occur in virtually any region of the vasculature including the aorta in the abdominal and thoracic regions. Aortic aneurysms are caused by hardening of the arteries (atherosclerosis), high blood pressure (hypertension), genetic disposition such as Marfan's Syndrome, trauma, or less common disorders. Atherosclerosis is the most common cause.

Where dilation meets or exceeds 50% of the original aortic diameter, i.e., where the diameter of the aorta is 150% of the original or expected diameter, intervention generally is deemed necessary. Without intervention, the aneurysm may continue to expand, leading to the possibility of tearing or rupture of the aorta, and death. Intervention includes techniques such as replacement of the aorta with a synthetic lumen which is sewn to the two ends of the still viable aorta after the aneurysmal portion has been opened or surgically removed, or, less invasively, by the endovascular placement of an exclusion device such as a stent graft across the aneurysmal site. The stent graft is a tubular member designed to provide a conduit enabling blood flow through the aorta without allowing the systemic pressure of the blood to further stretch the aneurysm. To enable these conditions, the stent graft must extend across the weakened blood vessel wall so that the opposed ends of the stent graft engage and seal against healthy blood vessel tissue to either side of the aneurysm.

A stent graft includes a stent framework (stent portion), which provides physical support of the stent graft in a tubular configuration once deployed at a vascular location, and a graft portion, comprising an excluding material, which is sewn or otherwise attached to the stent portion and which provides a relatively fluid-tight conduit for blood flow through the stent graft and past the aneurysm site. Insertion of a stent graft can be performed without a chest incision using specialized catheters that are introduced through arteries usually at a location in a leg adjacent the groin.

The aorta has numerous arterial branches. For example, the arch of the thoracic aorta has three major branches, all of which arise from the convex upper surface of the arch and ascend through the superior thoracic aperture to the root of the neck. The proximity of an aneurysm to a branch artery may limit the use of an excluding device such as a tubular stent graft, as the main body or ends of the tubular stent graft may occlude or block the branch arteries due to the need to position the stent graft to seal against a healthy, i.e., undiseased or dilated portion of the artery wall. There may be an inadequate length of healthy tissue for the stent graft to seal against in the area between the aneurysmal region of the artery and the location of the branch arteries, or, even if the stent graft initially is located without blocking a branch artery, there still is a risk of migration of the exclusion device to a position where it may partially or fully block a branch artery, since aneurysms of the descending aorta commonly occur above and adjacent to the celiac trunk, superior mesenteric and renal arteries.

Therefore, there is a desire in the art to achieve a greater success of aneurysm repair and healing, and in particular, mechanisms and methods to enable stent grafting or the placement of other exclusion devices adjacent to branch vessels in aneurysmal locations.

SUMMARY OF THE INVENTION

Embodiments according to the present invention address aneurysm repair and in situ positional stability of a device used for aneurysm repair. Specifically, embodiments according to the present invention provide methods and apparatus for use in the treatment of aneurysms located near branch vessels, using modular, sectional-type stent grafts that exclude the aneurysmal region without blocking or otherwise impeding the flow of blood to branch arteries. Additionally, these modular stent grafts provide a tight seal between sections. Although the specification provides specific configurations for use in abdominal and thoracic locations, stent grafts according to the invention are readily applicable to uses in other aneurysmal locations where branch vessels or other flow lumen discontinuities are present. Stent graft features according to the invention can also be used in all modular components of a stent graft that do not necessarily relate to branch vessels, including junctions between main modular elements and other stent graft extensions such as cuffs.

Thus, in one embodiment according to the invention there is provided a modular exclusion device useful for implantation in an aneurysmal site in a blood vessel having a branch vessel near the aneurysmal site comprising: a main body with at least one aperture; at least one insert with an insertion end, where a polymeric compound is disposed within the aperture of the main body, on the insertion end of the insert, or both within the aperture of the main body and on the insertion end of the insert, and where the polymeric compound comes into contact with both the aperture of the main body and the insertion end of the insert when the insertion end of the insert is disposed within the aperture of the main body. In addition, an embodiment provides a method of treating an aneurysm in a blood vessel having a branch vessel near the aneurysm, comprising deploying a modular exclusion device comprising a main body with at least one aperture; deploying at least one insert with an insertion end, where a polymeric compound is disposed within the aperture of the main body, on the insertion end of the insert or both within the aperture of the main body and on the insertion end of the insert, and where the polymeric compound comes into contact with both the aperture of the main body and the insertion end of the insert when the insertion end of the insert is disposed within the aperture of the main body.

BRIEF DESCRIPTION OF THE DRAWINGS

A more particular description of the embodiments may be had by reference to the embodiments according to the invention described in the present specification and illustrated in the appended drawings.

DETAILED DESCRIPTION

Reference now will be made to details of exemplary embodiments according to the invention. It is to be understood that the described embodiments are not intended to limit the invention solely and specifically to only these embodiments.

Methods and apparatus for stabilizing and treating an aneurysm include deploying a modular, sectional exclusion device, such as a stent graft, in the flow lumen of a blood vessel to span the aneurysmal location and seal off the aneurysmal location of the blood vessel from further blood flow while acting as a conduit to direct blood flow past the aneurysmal site. In the case of an aneurysm near a branch artery, methods and apparatus for treatment include positioning a modular endovascular stent graft in the aneurysmal site, where the stent graft includes a main body with at least one aperture, and in some embodiments two or three or more apertures, where separate individual inserts are disposed within each aperture to extend sealingly into the exclusion device and sealingly into a branch artery. A polymeric compound is used on either the insert, within the aperture or both, to ensure a snug, well-sealed fit between the aperture in the main body and the insert.

In addition to versatility in accommodating branch vessels, modular stents allow for in situ adjustment of insert lengths to accommodate different patient needs. Modular stent grafts are known in the art, and are disclosed in, inter alia, U.S. Pat. No. 6,129,756 to Kugler, et al.; U.S. Pat. No. 5,824,040 to Cox, et al.; U.S. Pat. No. 6,093,203 to Uflacker, et al.; U.S. Pat. No. 6,579,312 to Wilson, et al.; U.S. Pat. No. 5,906,641 to Thompson, et al.; and U.S. Pat. No. 5,855,598 to Pinchuk, et al., all of which are incorporated by reference in their entireties in for all purposes.

Each of the apertures of the main body of the stent graft is alignable with, and extendable into, a branch artery to aid in maintaining alignment of the aperture with the branch artery for providing additional positional stability for the deployed stent graft. The stent graft excludes the weakened vessel wall at the aneurysmal site from further exposure to blood flowing through the aorta, but, as a result of the aperture, allows blood to flow from the aorta to the branch artery(ies), even where the main body of the stent graft extends across the branch artery(ies). Inserts are then provided to fit sealingly into each aperture and further extend sealingly into the branch vessels, thereby preventing leakage of blood from the branch arteries into the region between the stent graft and the weakened blood vessel wall at the aneurysmal location. A polymeric compound strengthens the seal between the main body of the stent graft and the insert.

Figure 1:
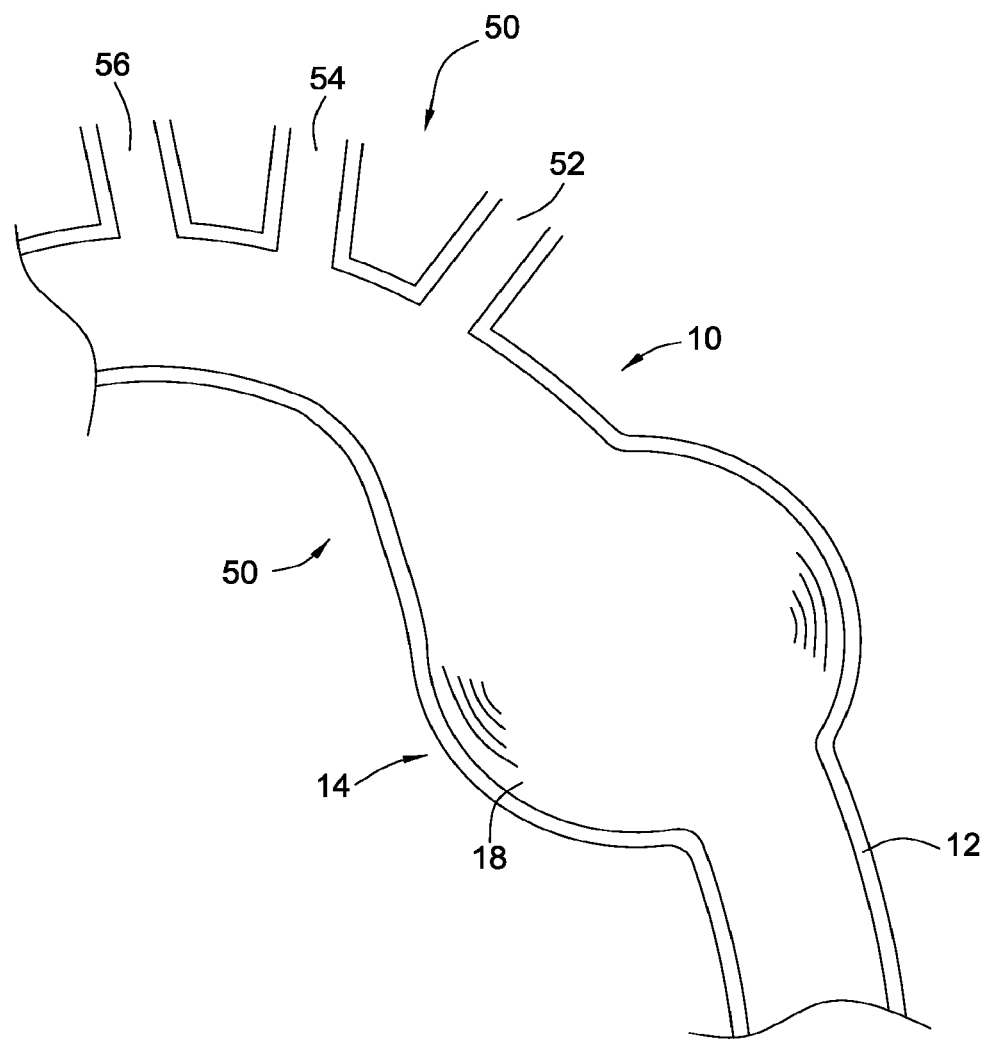
FIG. 1 is an artist's rendering of a cross section of an aorta showing an aneurysm near the thoracic aortic arch.

Referring initially to FIG. 1, there is shown an aneurysm of the abdominal aorta 10, such that the aorta is enlarged at an aneurysmal location 14 wherein the aorta wall 12 is distended and stretched. The aneurysmal location 14 forms an aneurysmal bulge or sac 18. If left untreated, the aneurysmal portion of the aorta wall 12 may continue to deteriorate, weaken, and eventually tear or burst. The aorta 10 extends upwardly from the heart (not shown), such that at the aortic arch 50, three branching arteries, the brachiocephalic trunk 56, the left common carotid artery 54 and the left subclavian artery 52, extend from aorta 10.

Figure 2A:
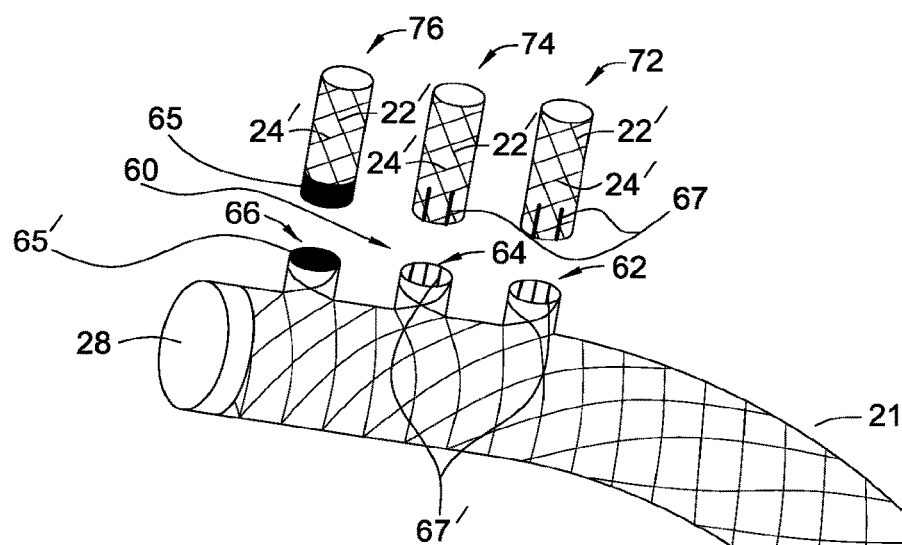
FIG. 2A shows an exterior side view of the stent graft useful for excluding the aneurysm of the aorta shown in FIG. 1.

FIG. 2A is an exterior side view of a modular stent graft that may be used to treat the aneurysm in FIG. 1 and that incorporates, as will be described further herein, a polymeric compound in one embodiment according to the present invention. There is shown generally a main body of the stent graft 20 comprising a tubular stent frame (framework) 22 and a graft material 24 attached to the stent frame 22 such as by sewing the graft material 24 to the stent frame 22, which together form an integral tubular structure having a profile substantially mimicking that of a healthy thoracic aorta. In one aspect, the stent frame 22 may be formed of a plurality of wires, each of the wires bent into a zig-zag configuration and joined at its opposed ends to form a continuous hoop. The individual wires are then interconnected by a plurality of spanning wires, which are crimped at their opposed ends which are crimped to adjacent formed wires to form the support structure of the stent frame 22. This support structure is attached to the graft material 24, such as by sewing the two portions together, and then positioned in the aorta to push against the aorta wall 12 and support the graft material 24 so as to enable the graft material 24 to seal against healthy portions of the aorta wall 12 and to provide a conduit through which blood flows and bypasses the aneurysmal location 14 of the aorta 10.

In the stent graft shown in FIG. 2A, there are three apertures (generically at 60) extending from the main body 21 of the stent graft 20, specifically apertures 62, 64 and 66, extending from the wall of the main body of the stent graft 20. Referring back to FIG. 1, when the stent graft 24 is deployed in the aorta 10, aperture 66 accommodates the exit of the brachiocephalic trunk 56 from the aortic arch 50, aperture 64 accommodates the exit of the left common carotid artery 54 from the aortic arch 50 and aperture 62 accommodates the exit of the left subclavian artery 52 from the aortic arch 50. In addition to the brachiocephalic trunk, the carotid artery and the left subclavian artery, other branched vessels (not shown) may be present and would be accommodated by one or more apertures as appropriate.

FIG. 2A also shows three inserts 72, 74 and 76, having both stent frame 22' and graft 24' components, i.e., each of the inserts 72, 74 and 76 are configured with a stent frame sized to be slightly larger than the circumference of the branch artery into which it is inserted, and has a tubular length of graft 24' material sewn or otherwise affixed thereto. Insert 76 is configured to be inserted into aperture 66 which accommodates the exit of the brachiocephalic trunk 56 from the aortic arch 50 and which supports the vasculature thereof; insert 74 is configured to be inserted into aperture 64 which accommodates the exit of the left common carotid artery 54 from the aortic arch 50 and which supports the vasculature thereof; and insert 72 is configured to be inserted into aperture 62 which accommodates the exit of the left subclavian artery 52 from the aortic arch 50 and which supports the vasculature thereof.

The materials making up the stent frame portion of the stent graft and/or insert(s) may be a metal, such as stainless steel, nitinol (NiTi) or tantalum (Ta), all known well in the art. In addition, various iron alloys such as iron platinum, iron palladium, iron nickel cobalt titanium, iron nickel carbon, iron manganese silicon, and iron manganese silicon chromium nickel. Generally the diameter of the metal wire/tube used for construction of the stent is between about 0.005 inches to about 0.02 inches. When nitinol is employed, the stent graft may have shape memory characteristics. While a braided construction of the stent frame is shown, this depiction is merely representative of any one of the numerous stent frame structures used to support stent grafts as is well known by persons skilled in the art.

The material composing the graft 24 of the stent graft 20 may be any biocompatible material that is mechanically stable in vivo, and is capable of preventing or substantially reducing the possibility of the passage or flow of blood or other body fluids there through. Typical materials for graft 24 include biocompatible plastics such as implantable quality woven polyester. Such polyester material may also include, therewith, components such as collagen, albumin, of an absorbable polymonomer or of a biocompatible fiber.

Additionally, non-resorbable elastomers or polymers such as silicone, SBR, EPDM, butyl, polyisoprene, Nitril, Neoprene, nylon alloys and blends, poly(ethylene-vinyl-acetate) (EVA) copolymers, silicone rubber, polyamides (nylon 6,6), polyurethane, poly(ester urethanes), poly(ether urethanes), poly (ester-urea), polypropylene, polyethylene, polycarbonate, polytetrafluoroethelene, expanded polytetrafluoroethelene, polyethylene teraphthalate (Dacron) polypropylene and polyethylene copolymers.

In the embodiments shown herein, where the stent graft 20 further includes apertures such as apertures 62, 64 and 66 which align with branch arteries adjacent to the aneurysmal site 14, and also receives an insert such as insert 72, 74 and 76 in each of the apertures, the inserts, and optionally the region of the apertures 62, 64 and 66 into which the inserts are received, may be formed of or coated with a non-resorbable polymer such as polymethylsiloxane, polydimethylsiloxane or polymethylphenylsiloxane or silicone. For example, each of the inserts 72, 74 and 76 may comprise a stent graft type structure, onto which a non-resorbable polymer, including polyurethane, silicone, polymethylsiloxane, polydimethylsiloxane or polymethylphenylsiloxane are coated thereon. The coating can be accomplished by sewing or adhering strips of the polymer to the mating surfaces of the inserts and apertures, by spray coating, by dip coating or vapor coating the materials thereon. Additionally, the inserts, and/or the apertures may be formed of a compound material formed, such as, for example, by insert molding wherein the aperture (62, 64 or 66) portions of the stent graft 20 are held in a mold and a polymer such as silicone is molded thereto. Where the stent frame 22 portion of the stent graft 20 is composed of a shape memory material, the material(s) selected to coat the apertures must also be able to withstand, without degradation of its mechanical properties which would render it incapable of sealing against itself, temperatures sufficiently low, on the order of the temperature of liquid nitrogen, to allow the tubular stent graft to be compressed into a small diameter structure for insertion into a delivery catheter as will be further described herein.

In one aspect, the non-resorbable polymer may be silicon, which is dip coated or insert molded to appropriate portions where the stent graft 20 and inserts 72, 74 and 76 engage one another in intended sealing contact. The silicone may be, for example, simply adhered to the stent graft 20 inner surfaces about the inner perimeter of the apertures 60, such as by lowering or placing the apertures 60 over a mandrel or rod having an as yet uncured, substantially viscous silicon located thereon. This could be performed, for example, by dipping the rod into a bath of uncured silicone, such that a film of silicone forms thereon, and mating the rod to the interior of the apertures. Likewise, the rod could be rolled over the exterior surface of the portion of the inserts 72, 74 and 76 which are to be received in the apertures, and thus the silicone will become adhered to, and thus deployed on, the surface of the inserts 72, 74 and 76. The silicone is then allowed to cure, either in air at atmospheric temperature and pressure conditions, or in an oven at elevated temperature.

The stent graft 20 and inserts 72, 74 and 76 of FIG. 2A show two different paradigms for use of the polymer on the components for sealing of the inserts 72, 74 and 76 to the apertures 60. Insert 76 and aperture 66 are coated with the polymer entirely about the circumferential mating or contacting position of the insert 76 to the aperture 66. In this case, the coating 65 extends entirely about the circumference of the insert 76 and from the end thereof which is received in the aperture 66 by a distance equal to the length by which the insert 76 is received in the aperture 66. Likewise, coating 65' is received in aperture 66 substantially about its entire projected length. In contrast, apertures 62 and 64, and likewise inserts 72 and 74, demonstrate a different aspect, in which a continuous circumferential coating of the polymer is replaced by a series of longitudinal stripes 67 extending along the outer surface of the inserts 72, 74 and stripes 67' of the polymer extend longitudinally along the inner surface of the apertures (aperture projection or nozzles) 62, 64 into which the inserts 72, 74 are received. In this aspect, the polymer stripes reduce the bulk of material and the circumferential stiffness of the stent graft, by leaving open spaces of bare graft material between the longitudinal stripes 67. Thus, in one example, such a configuration provides an alternate back and forth folding pattern as the stent graft diameter is reduced to its compressed state for delivery within the delivery system. In such a pattern when folded (compressed), the longitudinal stripes are not in contact with any adjacent longitudinal stripes, but only with the bare graft or stent frame materials, so that premature melding of polymer stripes to one another does not occur to cause sticking between adjacent folds when the stent graft is deployed (expanded). In this aspect, the inserts 72, 74, when received in their respective apertures 62, 64, are configured and positioned such that a portion of the stripes on the inserts 72, 74 contacts a portion of the stripe on the aperture.

The thickness of the graft material optionally is minimized to reduce the overall cross sectional thickness of the stent graft 20 and thus the size of the stent graft 20 as deployed in a delivery catheter. Generally, the graft material will be thinner than about 0.005 inch, and may be thinner than about 0.002 inch.

In the embodiment of the stent graft 20 shown in FIG. 2A, the ends of the graft material 24 extend beyond the marginal edges of the stent frame 22, i.e., the graft material 24 extends axially beyond the opposed generally circular ends of the stent frame 22 to form opposed ends 26, 28 of the stent graft 20. This arrangement is one of various arrangements of the position of the graft 20 portion with respect to the stent 22, as in other embodiments according to the present invention the ends of the graft portion 24 are coincident with the opposed ends of the stent frame 22 or the ends of the stent frame 22 may extend beyond the marginal ends of the graft portion 24. The ends of the graft portion 24 of the stent graft 20 are preferably configured to prevent fraying, which may be accomplished by heat fusion or binding of the edge of the graft portion 24 or by folding the end of the graft portion 24 back upon itself and sewing it to the stent frame 22 or to itself. Also, the graft portion 24 may be located on the interior of the stent frame 22, on the exterior of the stent frame 22, or the graft portion 24 may be located in the interstitial spaces between the portions or sections of the stent framework (shown as a braided pattern in the Figures herein). The graft portion 24 may include more than one layer or ply. The graft 24 preferably is sufficiently non-porous to prevent blood from leaking into the aneurysmal sac 18 (FIG. 1). In some embodiments, the material forming the graft portion 24 may include a coating of non-porous material over one or more porous layers. The graft portion 24 is attached the stent frame 22, typically as by sewing the graft 24 to the stent frame 22, but the use of an adhesive, heat bonding of the graft 24 to the stent frame 22, or other methodologies are specifically considered acceptable so long as the integrity of the connection of the graft 24 to the stent frame 22 is maintained.

Figure 2B:
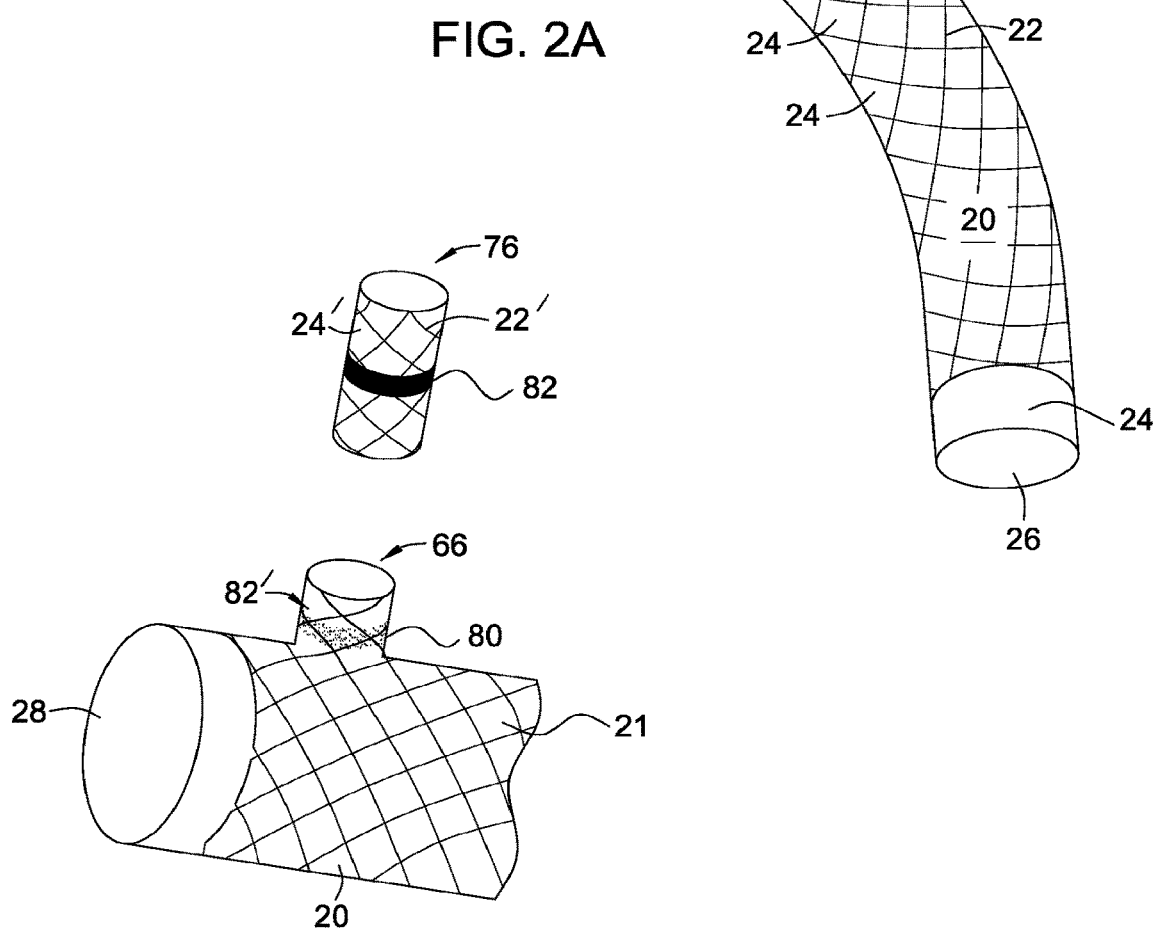
FIG. 2B is a close-up of one stent graft aperture and an insert therefore.

FIG. 2B is a close up of one example aperture 66' of the type shown in the group of apertures 60 formed on the main body 21 of the stent graft 20, and an example of an insert 76' of the plurality of inserts 72, 74 and 76 from FIG. 2A. In this embodiment, the inserts such as insert 76 shown in FIG. 2A are not coated with a polymer or other sealing and securing material, but instead a ring 82 of the sealing or securing material such as silicone is sewn or otherwise attached to the insert, and likewise a ring 82' of the sealing or securing material is secured within the inner circumference of the aperture 66' into which insert 76' is to be deployed. As shown in FIG. 2B, the aperture 66' (as well as similar adjacent apertures (not shown) like apertures 62, 64) preferably have a neck portion 80 which extends outwardly, in a tubular cross section, from the main body 21' of the stent graft 20', and includes a ring 82' formed thereon in the manner previously discussed. The insert 76' (and likewise adjacent inserts) is secured within the aperture 66' by friction between the conformable mating polymeric surfaces. In addition, where the material of the rings 82, 82' is a polymer having a low glass transition temperature, the area of contact between two adjacent rings 82, 82' will fuse together over time in situ (as it will in the other examples where polymer to polymer contact is described). Additionally, a portion of the insert 76 extends outwardly from the main body 21' of the stent graft beyond the end of the neck portion 80 of the aperture 66' and is positioned against the wall of the branch vessel into which it is deployed, preventing leakage of blood or other fluids past the apertures (e.g., 62, 64 and 66) of the stent graft 20, while allowing blood to flow through the inner tubular portion of both the apertures (e.g., 62, 64 and 66) and the inserts (e.g., 72, 74 and 76).

Figure 2C:
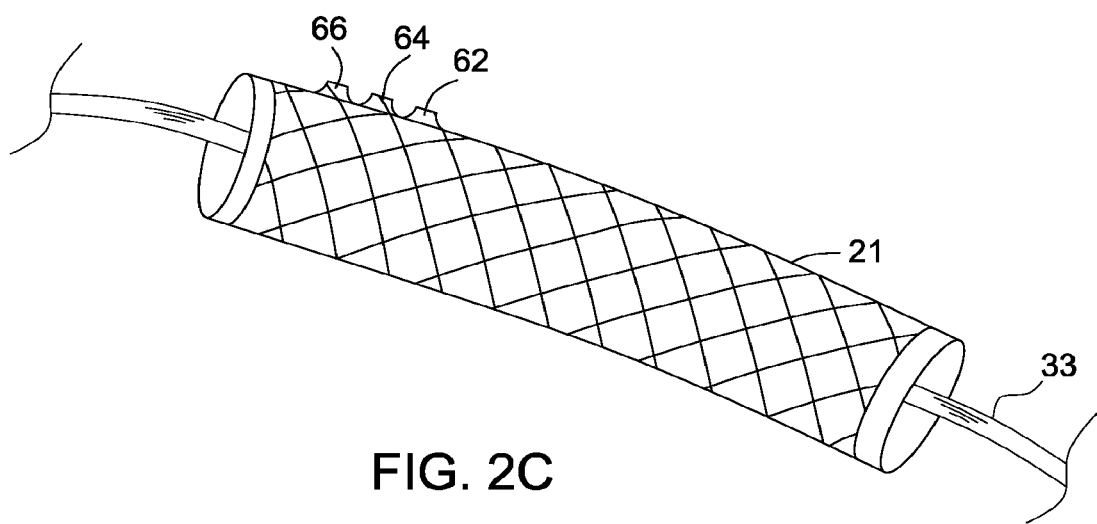
FIG. 2C is an exterior side view of the stent graft of FIG. 2A, wherein the stent graft has been located over a guidewire used for guiding the stent graft, once loaded into a delivery device, to the aneurysmal location in the thoracic aortic arch of FIG. 1.
Figure 2D:
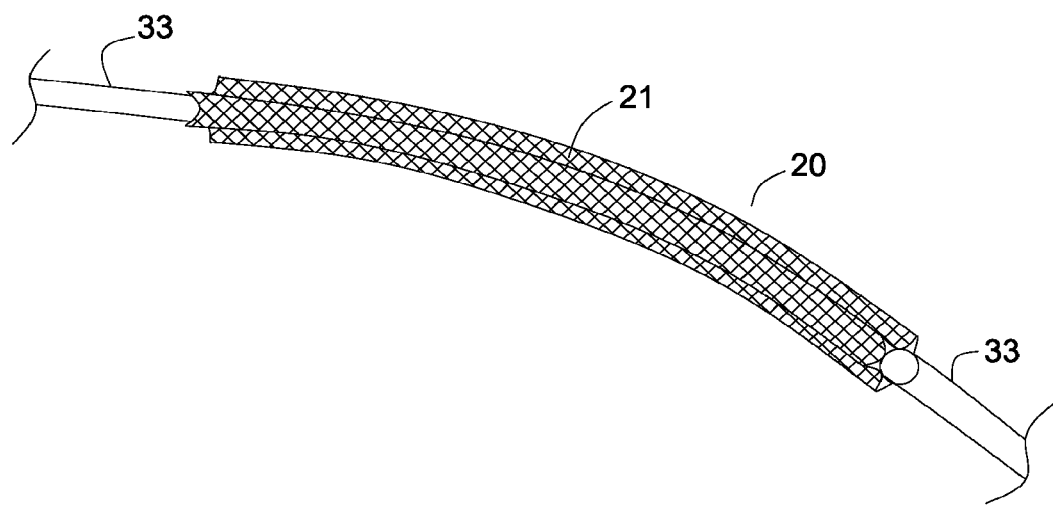
FIG. 2D is an exterior side view of FIG. 2C, wherein the stent graft has been compressed for delivery into the delivery device.
Figure 3:
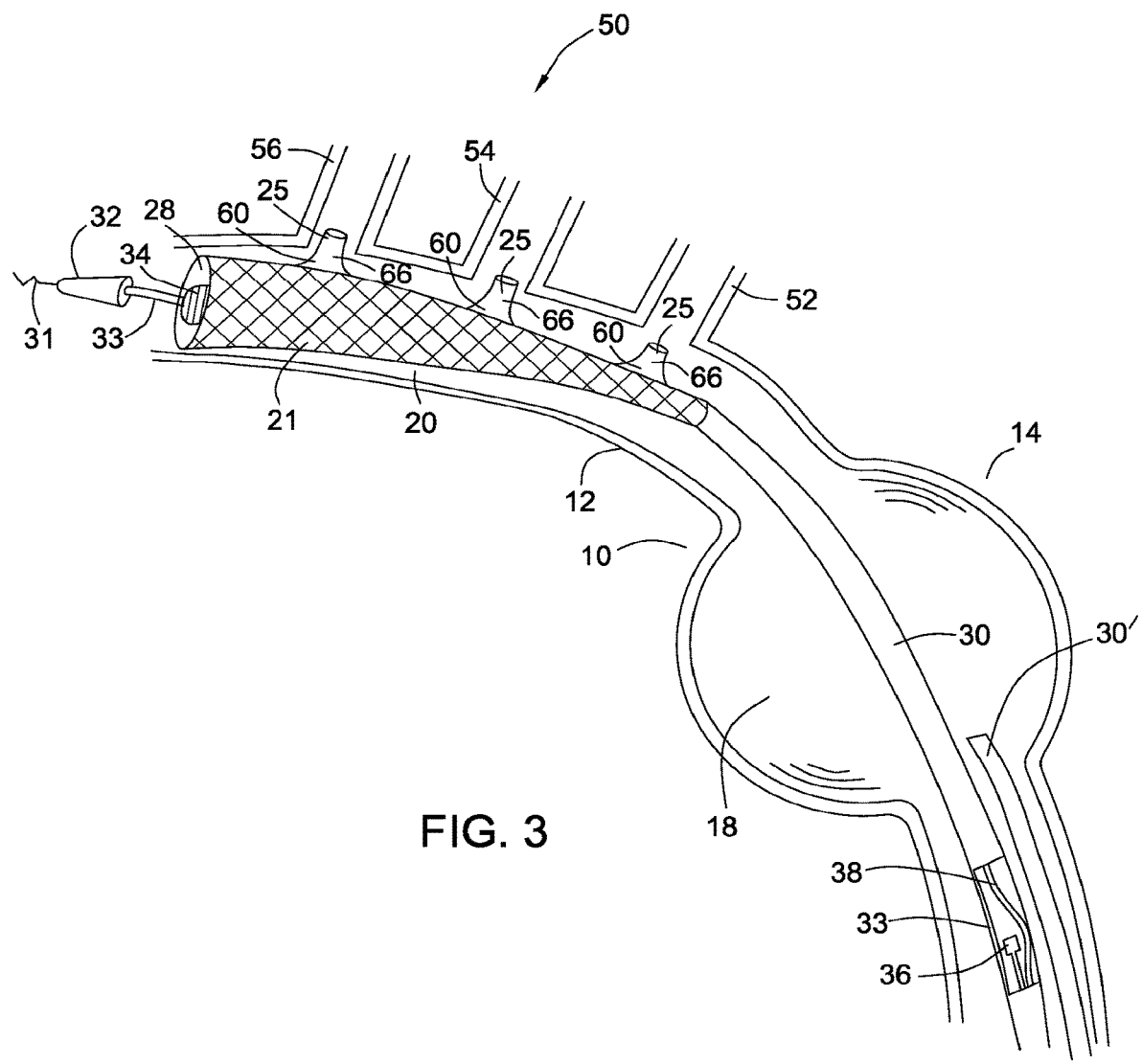
FIG. 3 is a cross sectional view of the aneurysmal aorta of FIG. 1 showing the deployment of a stent graft, with the stent graft delivery device displayed in partial cutaway.
Figure 3A:
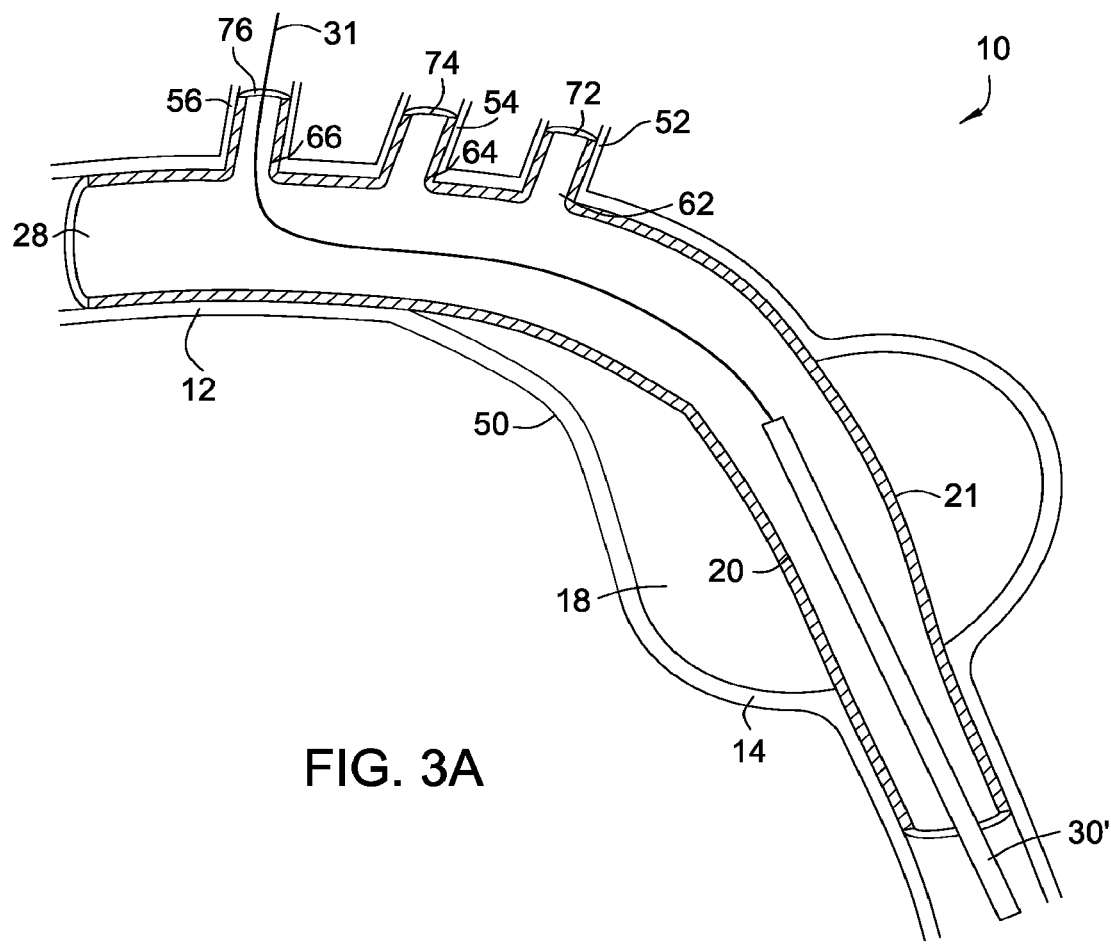
FIG. 3A shows a cross section of the main portion of the stent graft installed, with a catheter tracking to deliver a branch insert.

To deploy the stent graft 20 endovascularly, the stent graft 20 must be configured to fit within a tubular catheter. To accomplish this, the main body 21 of the stent graft 20 is first compressed, as shown in FIG. 2C, and then further folded or compressed to the configuration (diameter) of FIG. 2D at which time it may be inserted into the end of a catheter such as catheter 30 shown in FIG. 3. During the compressing of the stent graft 20, a guide wire catheter 33 may first be extended therethrough, as is also shown in FIG. 2C. The guidewire catheter 33 is a hollow tube through which a guidewire 31 (FIG. 3) is passed, and supports, at its distal end thereof, an insertion end 32 (catheter tip) through which guidewire 31 likewise extends (FIG. 3). For deployment of the stent graft 20, the guidewire catheter 33 extends within the length of the tubular catheter 30 such that its distal end is attached to the insertion end 32 and its proximal end is manipulable by a technician or surgeon to position the distal end in relative proximity of the deployment location. Where the stent frame 22 portion of the main body 21 of the stent graft 20 is configured of a shape memory material, such as nitinol, the main body 21 can be first cooled to a very low temperature, such as by using sprayed bursts of liquid nitrogen which depending on the composition of the nitinol can make the nitinol plastically deformable an easier to load, before it is compressed (as shown in FIGS. 2C and 2D.) Where the stent portion 22 is comprised of a non-shape memory material, an inflation device such as a balloon 34 on the guidewire catheter 33 connected to an end of an inflation lumen 38 extending along the guidewire catheter 33 is first located inside of the tubular shape of the main body 21, onto which the stent graft can be compressed. Likewise, inserts 72, 74 and 76 can be compressed and placed in separate catheters, one such catheter shown as catheter 30' in FIG. 3A. Each insert may be located in a single catheter, or all of the inserts necessary to deploy one into each of the apertures 60 may be deployed in a single catheter, with one insert closest to the open end thereof, and the next one(s) stacked therebehind. Additionally, where the inserts are configured incorporating a non-shape memory alloy as the stent material, a balloon must be first placed inside the tubular volume before compressing it. This can be unnecessary where the insert is self expanding. It is also possible that the insert is compressed over the smaller balloon and is able to adhere to the balloon without the use of an outer sheath.

Referring still to FIG. 3, the initial deployment of the stent graft 20 into the thoracic arch into an aneurysmal location 14 spanning position is shown. Prior to the deployment of the stent graft 20, a guide wire 31 is extended from a remote blood vessel incision site leading to the arch 50, and through the arch 50, such that the inserted end thereof extends past the intended location of the deployed stent graft 20. To position and properly locate the stent graft 20 in a spanning, sealed position in the aneurysmal location 14, the stent graft 20 is introduced through an artery, such as the femoral artery (not shown), by inserting the catheter 30 into the artery through an incision in the leg. The catheter 30 preferably includes an outer sheath portion enclosing a collapsed or compressed stent graft 20 held within a distal end of the sheath 30 which is introduced into the patient's artery and from which the stent graft 20 is deployed. A proximal end of the catheter (not shown) is maintained external to the body and is manipulated to axially and rotationally position catheter within the aorta 10. At least one push rod 36 can extend within the catheter 30, from a position adjacent to the distal end of the stent graft 20 within the hollow portion of the catheter 30, to a position beyond the proximal end of the catheter 30. Additionally, where a balloon is employed in the deployment of the catheter, a lumen 38 capable of introducing saline extends from a balloon 34 within the stent graft 20 to a position beyond the proximal end of the catheter 30 where it is connectable to an inflation device. Catheter 30 and any other catheters required for deployment typically carry radiological markers on their outer surface adjacent the deployment end 38, to enable the surgeon deploying the stent graft to determine the position of the catheter in the body, such as by fluoroscopic or other means. Additionally, the stent graft 20 has radiological markers thereon to enable determination of the position and rotational orientation thereof at the aneurysmal location.

In deploying the stent graft 20, catheter 30 is tracked through the patients' artery, until the end thereof is disposed in the arch physically beyond the aneurysm location 14. The push rod 36 which is located against the distal end of the stent graft 20 within catheter 30, and holds the stent graft 20 stationary as the tubular sheath of the catheter 30, is withdrawn or retracted with respect to the aneurysmal location 14. As the sheath retracts, the stent graft 20 is progressively released from the sheath in a position spanning across the aneurysmal location 14 of the aorta. As the catheter sheath is withdrawn with the push rod 36 held stationary, and as the deployment of the stent graft 20 is beginning, the catheter 30 may be rotated to ensure that the main body 21 of the stent graft 20 deploys with the apertures 62, 64 and 66 in alignment with the branch arteries 52, 54 and 56.

The stent graft apertures 62, 64, and 66 are, when the stent graft 20 is properly aligned in the aorta 10 and arch 50, aligned with the branch arteries 52, 54 and 56, and expanded to extend outwardly from the wall of the stent graft 20. In the configuration of the embodiment of the stent graft in FIGS. 2A and 3, three branch arteries must be spanned and thus three apertures 60 are provided. Alternatively, where the size and location of the aneurysmal sac 18 enables a shorter length of stent graft to ensure sufficient sealing of the stent graft against the wall of the aorta, or, where the aneurysmal sac is more remotely located from the branch artery locations, the stent graft may be deployed with fewer openings therein, and an aperture 60 need only be located in each of those openings. After the main body 21 of the stent graft 20 is deployed, the balloon, where used, is deflated and withdrawn along with the catheter 30.

A separate catheter, e.g., 30', may be used to deploy each insert 72, 74 and 76 into each separate aperture 62, 64 and 66. This is provided by deploying additional catheters in a number equal to the number of inserts used, through the artery and within the stent graft 20, and extending each catheter along a guidewire into individual stent graft branches 60. To direct the catheters into the appropriate apertures 60, a guide wire 31' is first deployed and guided into and past the appropriate aperture and a further distance along the appropriate branch artery 52, 54 or 56. The catheter is positioned such that the distal end of the catheter is disposed inside of the aperture and branch vessel where the insert in the branch vessel will be located. As with the deployment of the main body 21, the sheath of the catheter 30', with a push rod (not shown) positioned against an insert 72, 74 or 76, is withdrawn and the insert 72, 74 or 76 deploys, with the shape memory material expanding to the expanded diameter of the tubular section of the insert 72, 74 or 76, with the outer surface thereof engaged with the inner surface of the aperture to sealingly secure the insert 72, 74 or 76 therein by an interference or friction fit, with the portion extending outwardly therefrom in sealing engagement with the adjacent wall of the particular branch vessel 50 into which it is deployed. Where shape memory material is not used, a balloon is positioned within the insert 72, 74 or 76, to cause its expansion. This procedure is repeated, with repositioning of the guidewire and redeployment of the catheter 30', until all of the needed inserts are deployed. Once the stent graft main body 21 and inserts 72, 74 and 76 are deployed, all balloons (where needed) are deflated, the catheters and guidewires are withdrawn, and the artery and leg incision(s) are closed. The stent graft 20 and inserts 72, 74 and 76 are thus positioned, spanning the branch arteries without blocking them. Methods and apparatus for the deployment of sectional stent grafts are also disclosed in U.S. Pat. No. 5,683,451 to Lenker, et al.; U.S. Pat. No. 5,713,917 to Leonhardt, et al.; and U.S. Pat. No. 5,984,955 to Wisselink, et al., all of which are incorporated by reference in their entireties in for all purposes.

Once the inserts 72, 74 and 76 are positioned in the respective apertures 62, 64 and 66, the contacting surfaces of the polymer disposed on both the apertures 62, 64 and 66 and the inserts 72, 74 and 76 provide both sealing of the insert-aperture interface, but likewise provide increased friction due to the polymer to prevent the movement of the inserts with respect to the apertures. Over time, the interface of the (polymer) sealing materials may meld together to form a continuous adhering material between the insert and the aperture. However, the ability of these materials to meld together is, in part, based upon their tackiness, i.e., the ability or desire of the material to stick to materials into which it comes in contact. This property may affect the ability to deploy the apertures 62, 64 and 66 and the inserts 72, 74 and 76, as the sealing and securing material thereon, for example the coating 65 or 65', may come into contact with itself during the compressing of the stent graft 20 or the inserts 72, 74 and 76 for the placement thereof into catheters. To minimize the risk that the apertures of the stent graft 20 or the inserts 72, 74 and 76 will become adhered together in the collapsed state, three construction and/or deployment paradigms may be used: Firstly, a balloon may be provided within the envelope of each of the apertures 62, 64 and 66 and inserts 72, 74 and 76, such that the inflation thereof, in situ, will overcome any sticking of the material 65 to itself. Secondly, the sealing and securing material may be comprised as stripes 67, 67', as shown in FIG. 2A, such that upon compressing of the stent graft 20 or the inserts 72, 74 and 76, the stripes 67, 67' of sealing and securing material contact stent 22 or graft 24 material, and not an adjacent stripe 67, 67'. Thirdly, the coating 65, 65' may, prior to the compressing and configuring of the stent graft 20 and the inserts 72, 74 and 76, be covered with a release, material, such as a thin sheet of PTFE or FEP material, which material is adhered likewise to a wire or other catheter deployable member which can be pulled outwardly of the patient, during the deployment of the stent graft 20 or inserts 72, 74 and 76, to pull the sheet off of the polymer prior to the contact of the polymer carrying portion of the insert 72, 74 or 76 with its appropriate aperture 62, 64 or 66. Thus, the stickiness or tackiness of the polymer may be used to help secure and seal or meld the insert and aperture together, while the inserts 72, 74 and 76 and apertures 62, 64 and 66 are expandable in situ.

Figure 4:
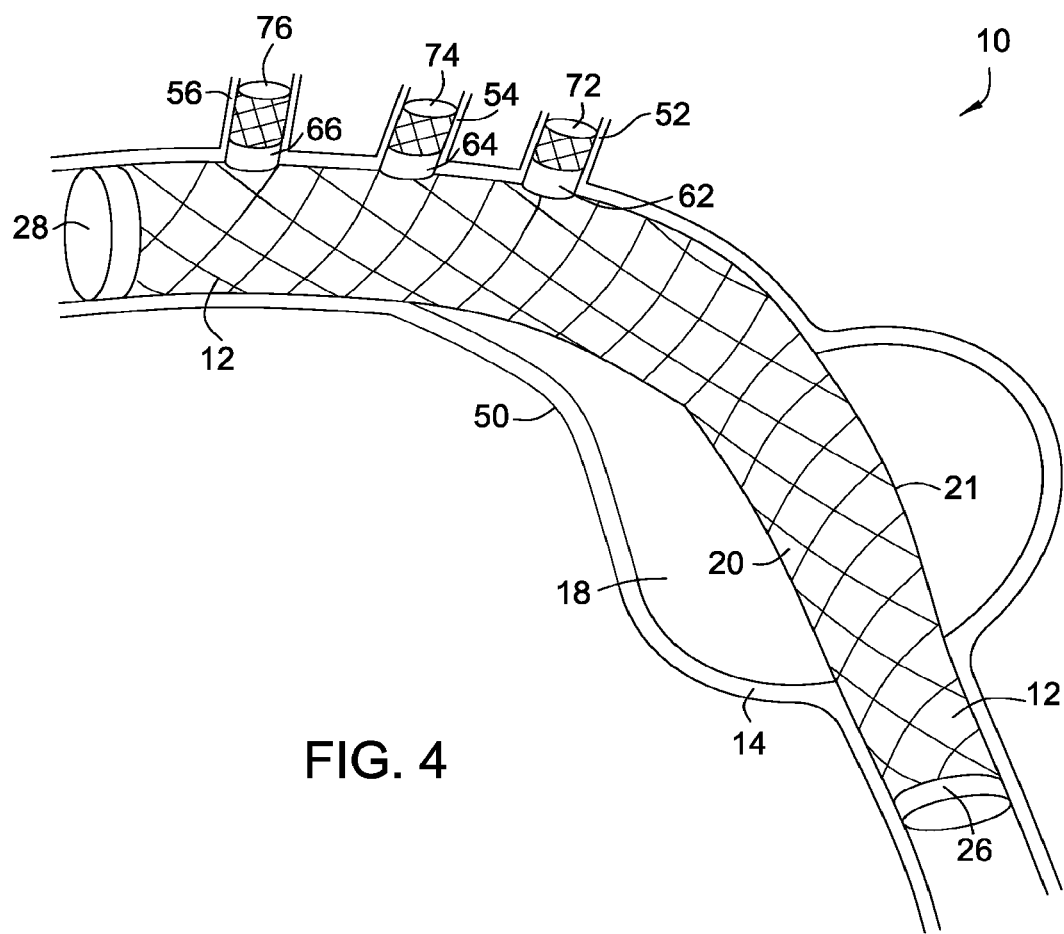
FIG. 4 is an exterior side view of the stent graft of FIG. 2 shown deployed in the aneurysmal aorta of FIG. 1 and further showing extension of the apertures and the inserts from the upper wall of the stent graft into the branch arteries of the aneurysmal aorta of FIG. 1.
Figure 5:
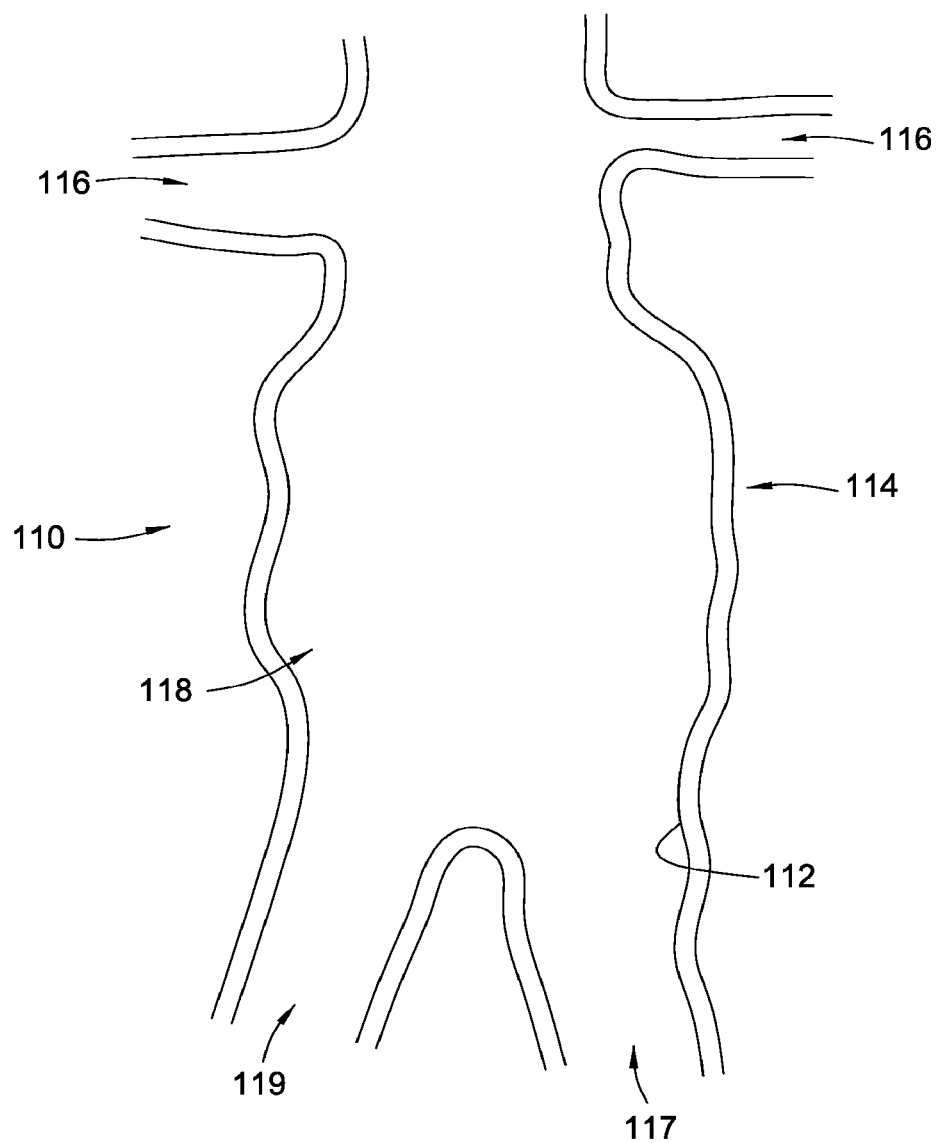
FIG. 5 is an artist's rendering of a cross section of an aorta showing an aneurysm of the abdominal aorta.

Referring to FIG. 4, once deployed, the stent graft 20 is intended to provide a flow conduit across the aneurysmal sac 18 of the aorta 10, and to seal off the aneurysmal sac 18 from further blood flow. The stent graft 20 is sized so that, upon deployment in the aorta 10, the diameter of the stent graft 20 is slightly larger than the normal, healthy diameter of the aorta 10 so that the opposed ends 26, 28 of the stent graft 20 are in apposition with the inner wall of the aorta 10. Further, the stent graft 20 is long enough to span the aneurysmal sac 18 of the aorta 10 and sealingly contact the aorta wall 12 on opposite sides of the aneurysmal sac 18. Such sealing includes the region of the aorta wall 12 between the branch arteries 52, 54 and 56, as well as regions distal and proximal from the aneurysmal region 18. To enable sealing by the stent graft 20, the stent graft includes a circumferential wall, which, at opposed ends 26 and 28, is engageable against the inner wall 12 of the aorta 10 to effect sealing and prevent, when properly deployed, blood flow into the aneurysmal sac 18 of the aorta 10. Additionally, the inserts 72, 74 and 76 extend into the branch arteries 52, 54 and 56, providing an extended conduit for blood flow thereby excluding blood from the region of the branch vessels where vessel delamination (dissection) may occur.

Where FIG. 1 shows an aneurysm near the thoracic aortic arch, FIG. 5 is an artist's rendering of an aorta showing an aneurysm in the abdominal aorta. FIG. 5 shows an aorta 110 with an aortic wall at 112. There is an aneurysmal site at 114, defining an aneurysmal sac at 118. Renal arteries are seen at 116, the right iliac artery is seen at 119 and the left iliac artery is seen at 117.

Figure 6A:
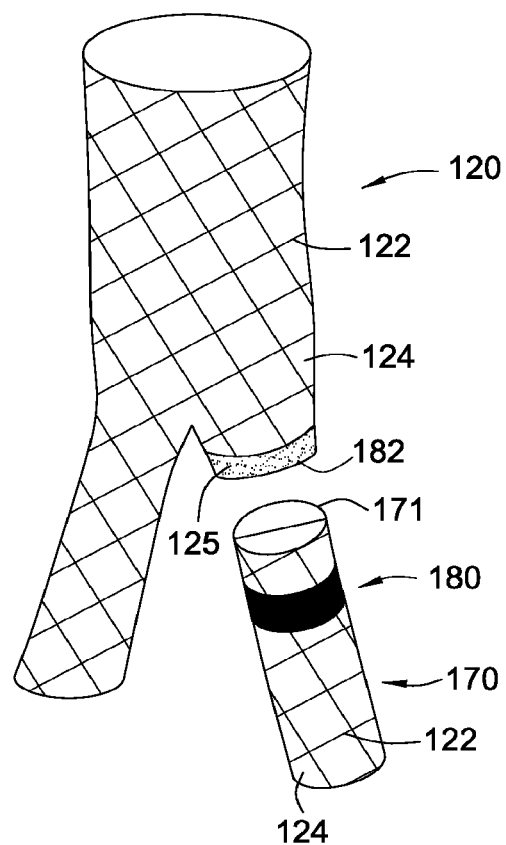
FIGS. 6A and 6B are exterior side views of a stent graft useful for excluding the aneurysm of an abdominal aorta as shown in FIG. 5.
Figure 6B:
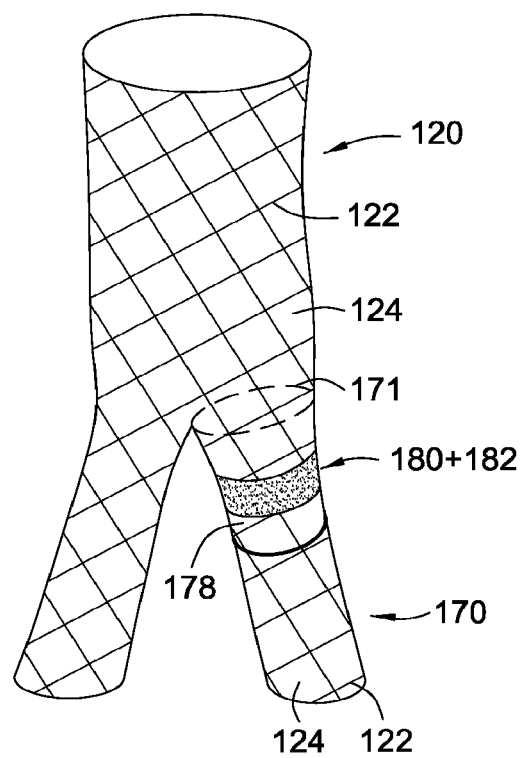

FIGS. 6A and 6B are schematic exterior side views of a stent graft useful for excluding an aneurysm of the aorta shown in FIG. 5. FIG. 6A shows a main body of the stent graft 120 generally, with a stent frame 122 and graft portion 124. In addition, stent graft 120 has a second branch insertion site 125, as well as a polymeric compound 182 such as a polymeric compound such as that used in conjunction with the inserts and apertures of the embodiment shown in FIGS. 2, 3 and 4 disposed inside the insertion site (shown in phantom). Also in FIG. 6A, there is an insert 170 having an insertion end 171, likewise comprised of a stent frame portion 122 and graft portion 124. On insert 170, there is disposed, at 180, a polymeric compound such as that used in conjunction with the inserts and apertures of the embodiment shown in FIGS. 2, 3 and 4.

FIG. 6B shows the main body of the stent graft 120 and insert 170 of FIG. 6A assembled. In FIG. 6B, insertion end 171 of insert 170 is disposed within the main body of the stent graft 120, such that the polymeric compounds 180, 182 on the insert 170 and the main body of the stent graft 120 engage against one another.

Figure 6C:
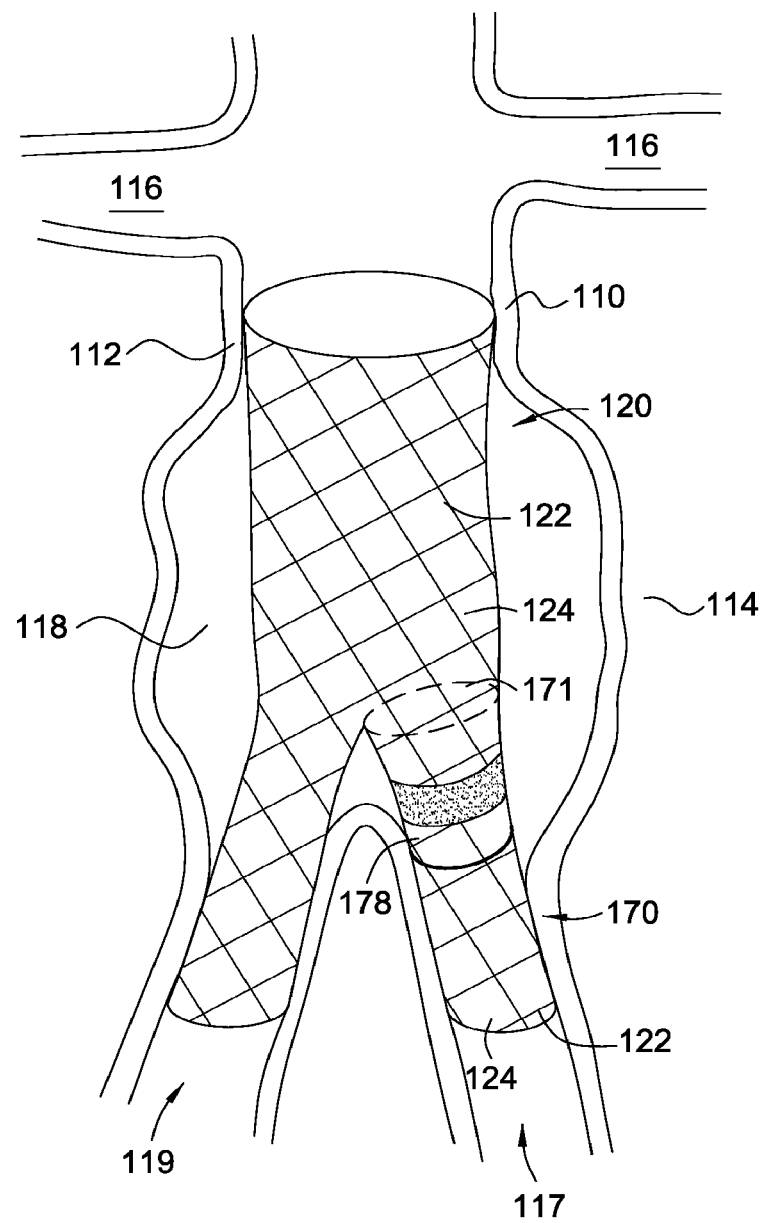
FIG. 6C shows the stent graft of FIGS. 6A and 6B positioned in an abdominal aorta.

FIG. 6C shows the assembled stent graft and insert from FIG. 6B positioned within an abdominal aortal region of FIG. 6A. The aorta 110 shows an aorta wall at 112, an aneurysmal region at 114 and an aneurysmal sac at 118. The renal arteries are seen at 116, the left iliac artery is seen at 117 and the right iliac artery is seen at 119. Stent graft 120 and insert 170 are shown with stent portions 122 and graft portions 124. The insertion end of insert 170 is shown at 171. The stent graft 120 and insert 170 are deployed similar to how stent graft 20 shown in FIGS. 2, 3 and 4 is deployed, i.e., the main body stent graft 120 is tracked, in a catheter, up the right iliac artery 119, and deployed from the catheter and positioned as shown in FIG. 6C. The insert 170, which forms the contralateral leg of the assembled stent graft, is tracked in a catheter up the left iliac artery 117, such that the end thereof having the polymeric compound 180 thereof is inserted into the opening 125 of the stent graft 120, and then inflated or otherwise restored to its free state such that polymer portions 180 and 182 contact one another.

Figure 7A:
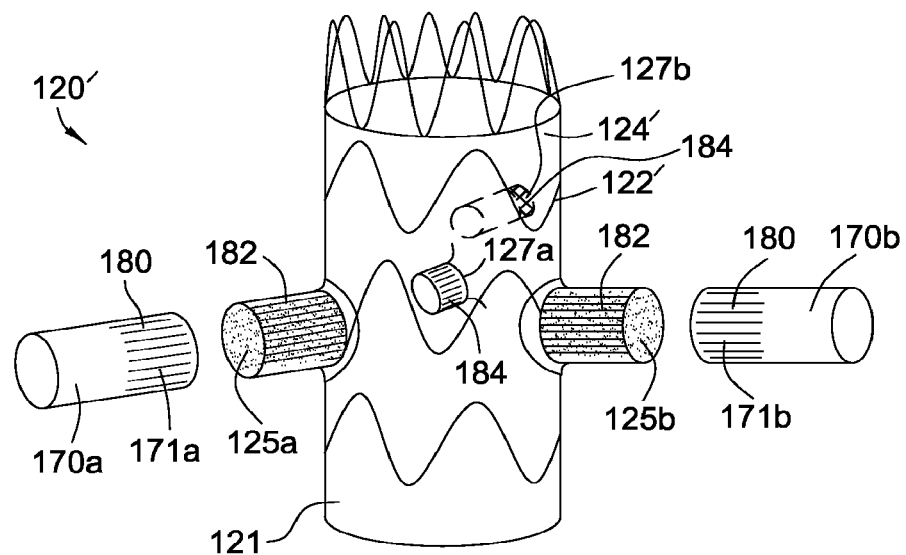
FIG. 7A is an exterior side view of another stent graft useful for excluding the aneurysm of an abdominal aorta as shown in FIG. 5.

FIG. 7A is an exterior side view of an upper portion of an example of a custom configured stent graft useful for excluding an aneurysm of an aorta as shown in FIG. 5. FIG. 7A shows a main body of a stent graft 120' generally, with stent frame/support portions 122' and graft portions 124'. In addition, stent graft 120' has branch insertion sites 125a and 125b that extend radially outwardly from the stent graft 120' and which align with the renal arteries (not shown) when the stent graft 120' is deployed. Polymeric compound 182, such as the polymeric compound used in conjunction with the inserts and apertures of the embodiment shown in FIGS. 2, 3 and 4, is disposed inside the insertion sites 125a and 125b. Also shown in FIG. 7A, are inserts 170a and 170b having mating ends 171a and 171b, on which is disposed the polymeric compound at 180. The embodiment of the stent graft 120' of FIG. 7A further includes two fenestration extensions at 127a, 127b with the polymeric compound 184 disposed on the outer surface thereof. The fenestration extensions accommodate the celiac trunk and the superior mesenteric artery (not shown) when the stent graft 120' is deployed.

Figure 7B:
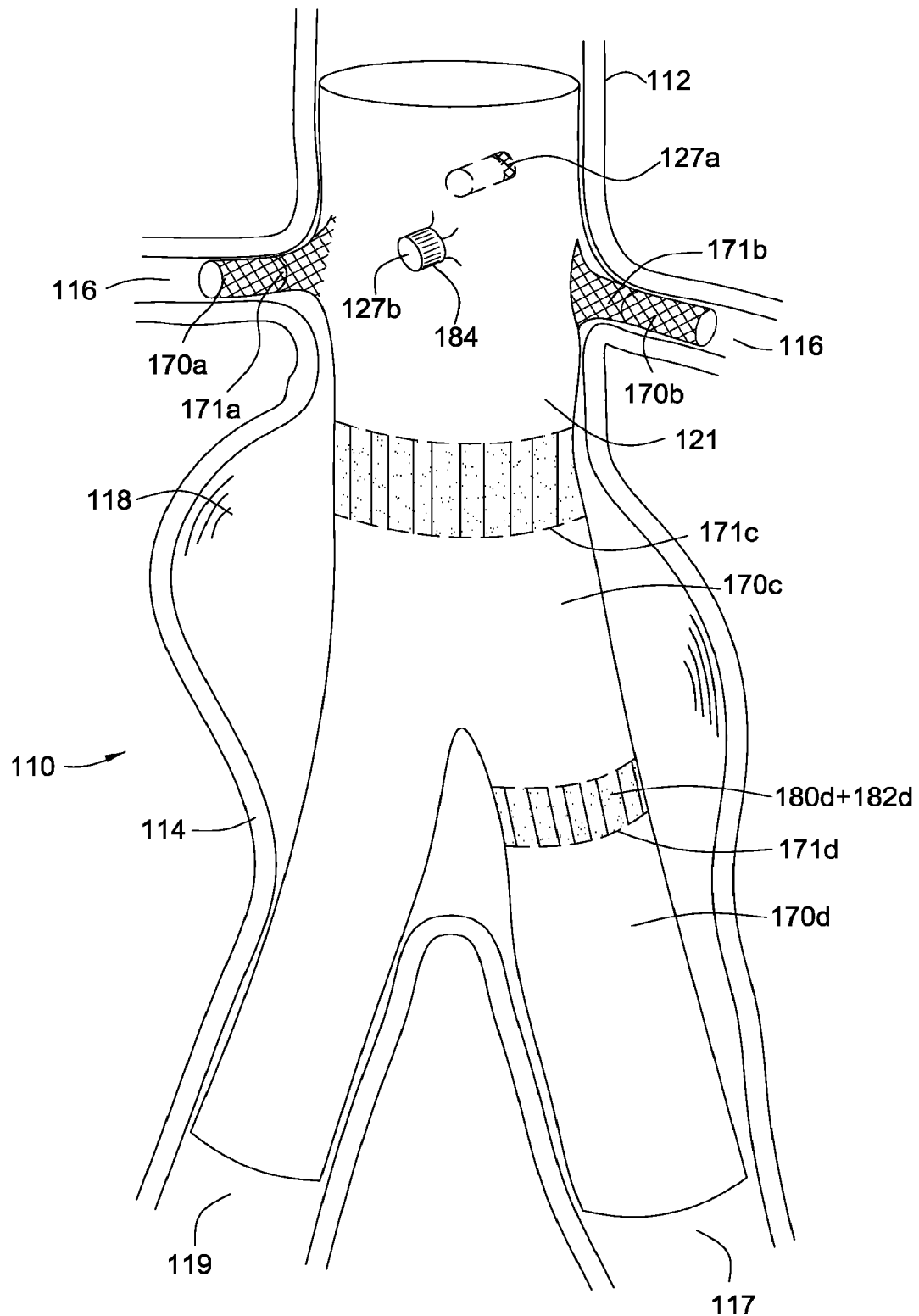
FIG. 7B shows the stent graft of FIG. 7A positioned in an abdominal aorta.

FIG. 7B shows the upper portion of the stent graft 120' from FIG. 7A assembled with two additional portions positioned within an abdominal aortal region. The aorta 110 has an aorta wall at 112, an aneurysmal region at 114 and an aneurysmal sac at 118. Renal arteries are seen at 116, the left iliac artery is seen at 117 and the right iliac artery is seen at 119. The stent graft 120' consists of five portions: an upper portion 121 along with inserts 170a and 170b seen in FIG. 7B, as well as inserts 170c attached to the open lower end of upper portion 121 and including a leg which accommodates right iliac artery 119, and an insert 170d which forms a leg and extends from an opening in the insert 170c into sealing engagement with the left iliac artery 117. Inserts 170a, 170b, 170c and 170d each have insertion ends 171a, 171b, 171c and 171d, respectively, with the polymeric compound disposed thereon.

In addition, FIG. 7B shows fenestration extensions 127a, 127b from FIG. 7A. Fenestration extension 127a accommodates the superior mesentery artery (not shown), and fenestration extension 127b accommodates the celiac trunk (not shown). Polymeric compound 184a and 184b is disposed on the outer surface of the fenestration extension to provide enhanced sealing of the fenestration extension with the branch arteries.

Figure 8A:
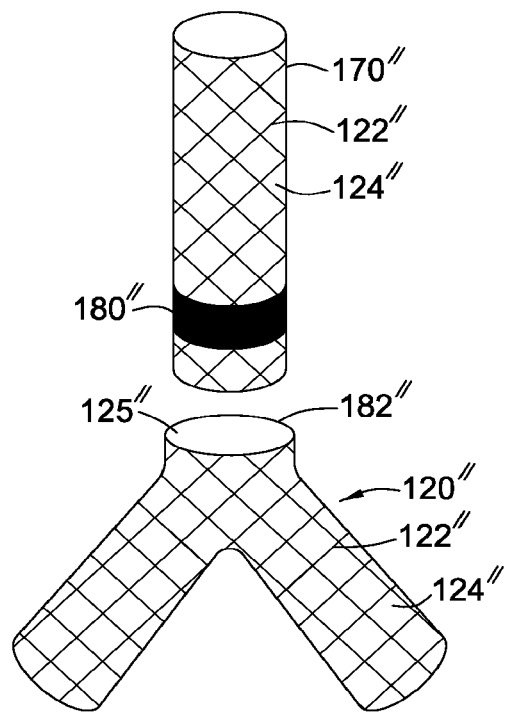
FIGS. 8A and 8B are exterior side views of yet another stent graft useful for excluding the aneurysm of an abdominal aorta as shown in FIG. 5.
Figure 8B:
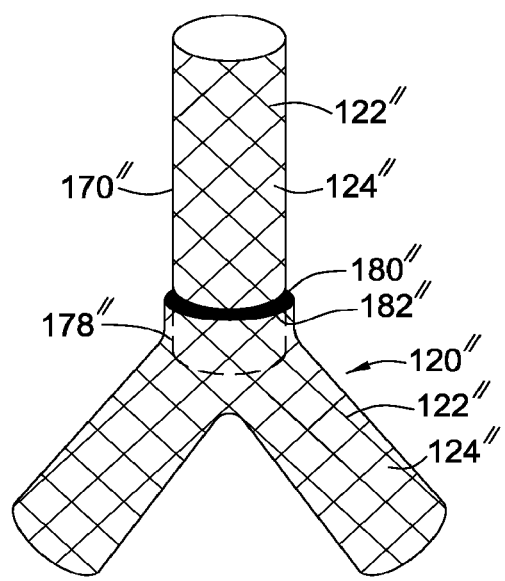

FIGS. 8A and 8B are exterior side views of yet another configuration of stent graft useful for excluding the abdominal aorta shown in FIG. 5. FIG. 8A shows a main body 120" of a stent graft and an insert 170". Again, both the main body 120" of the stent graft and insert 170" have stent portions at 122" and graft portions at 124". The main body 120 shows an insertion site 125 for insert 170" as well as polymeric compound 182", a polymeric compound such as that used in conjunction with the inserts and apertures of the embodiment shown in FIGS. 2, 3 and 4, disposed within the inside rim of the insertion site. Insert 170" shows an insertion end at 171" as well as the polymeric compound at 180" shown applied around the insertion end. FIG. 8B shows the main body 120" of the stent graft and the insert 170" of FIG. 8A assembled. Again, stent frame 122" and graft 124" portions are seen on both the main body 120" of the stent graft and the insert 170". In addition, a portion of the insert 170" is shown in phantom 178" disposed within the stent graft 120. Polymeric compounds 180 and 182 are seen in phantom as well.

Figure 8C:
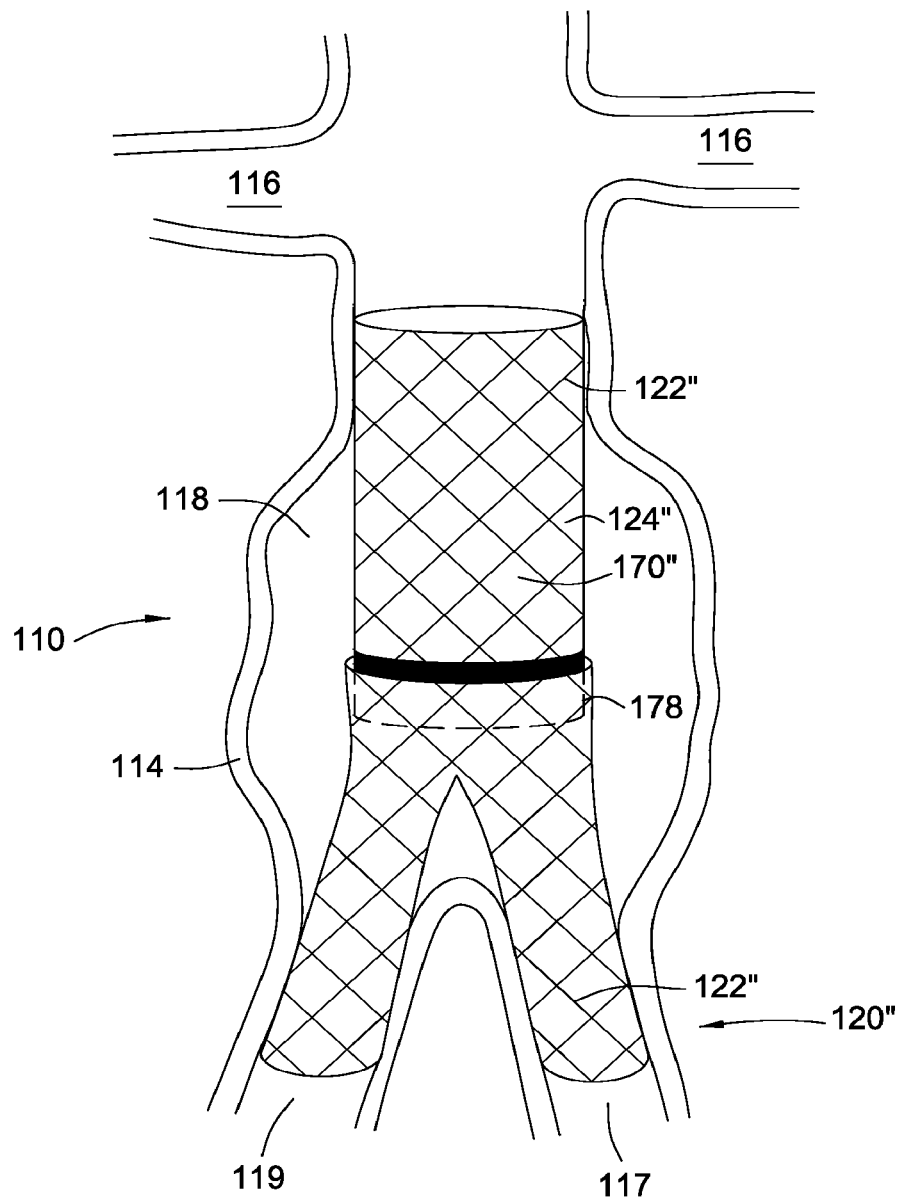
FIG. 8C shows the stent graft of FIGS. 8A and 8B positioned in an abdominal aorta.

FIG. 8C shows the assembled stent graft/insert combination of FIG. 8B positioned within an abdominal aneurysm. Again, an aorta is seen at 110, an aortal wall is seen at 112, an aneurysmal region is seen at 118 and an aneurysmal sac is seen at 118. Renal arteries are shown at 116, the left iliac artery is shown at 117 and the right iliac artery is shown at 119. Main body 120" of stent graft and insert 170" are also shown.

Figure 9:
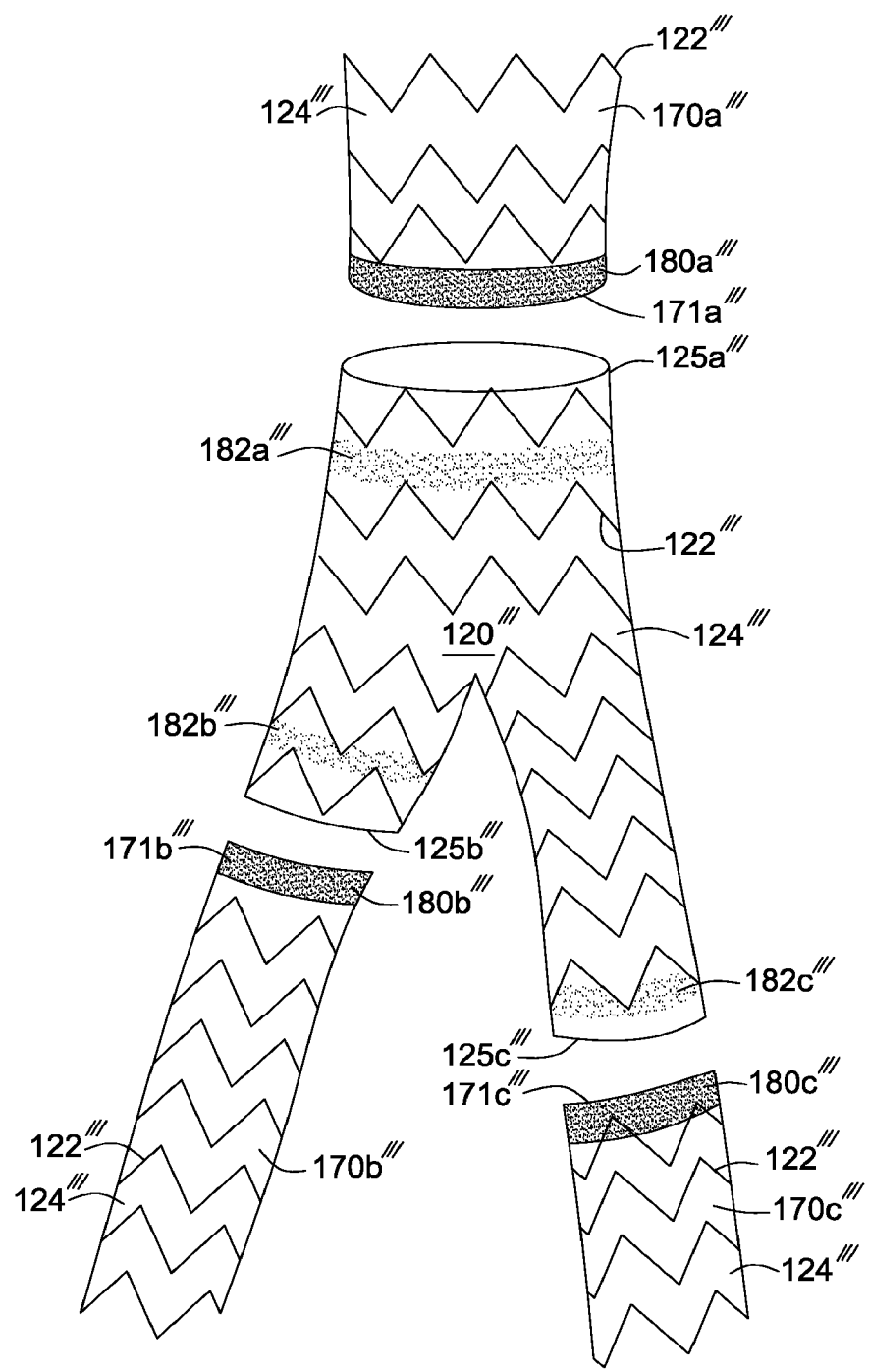
FIG. 9 is an exterior side view of another modular, multi-sectional stent graft useful for excluding the abdominal aortic aneurysm shown in FIG. 5.

FIG. 9 is an exterior side view of yet another stent graft useful for excluding the aneurysm of the abdominal aorta shown in FIG. 5. FIG. 9 shows a four-piece modular stent graft, with a main body at 120" and inserts at 170a''', 170b''' and 170c'''. Stent 122''' and graft 124''' portions are shown on each of the four modular pieces. Insertion end 171a''' of insert 170a''' is shown, as is insertion end 171b''' of insert 170b''' and insertion end 171c''' of insert 170c'''. Polymeric compound, a polymeric compound such as that used in conjunction with the inserts and apertures of the embodiment shown in FIGS. 2, 3 and 4, is shown disposed on the inserts at 180a''', 180b''' and 180c'''. In addition, polymeric compound such as silicone is shown disposed within stent graft main body 120''' in phantom at 182a''', 182b''' and 182c'''.

Figure 10:
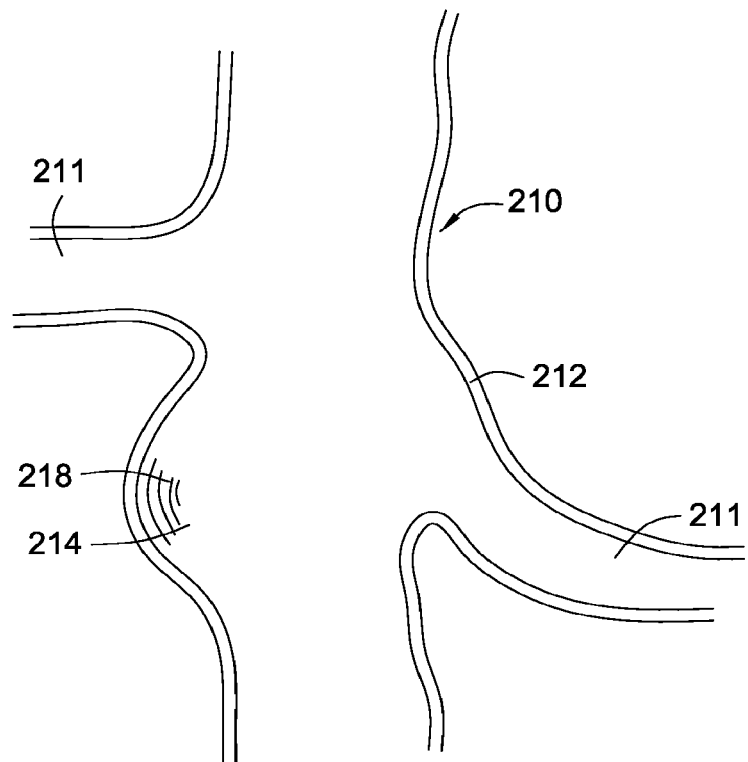
FIG. 10 is an artist's rendering of a cross section of a blood vessel showing an aneurysm in a branched portion of a blood vessel.

FIG. 10 is an artist's rendering of a blood vessel showing an aneurysm adjacent a branch portion of the vessel. FIG. 10 shows an aorta at 210, having aortal branches at 211. The aortal wall is seen at 212, the aneurysmal site is seen at 214 and the aneurysmal sac is seen at 218.

Figure 11A:
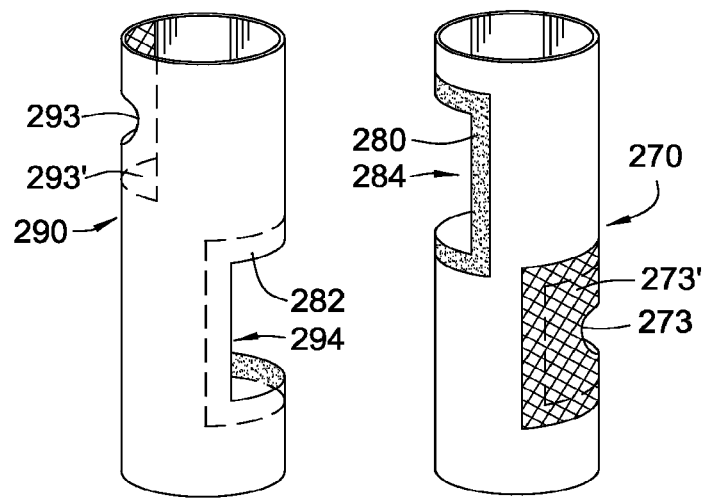
FIG. 11A is an exterior side view of two parts of a rotation cuff device useful for excluding the aneurysm of the vessel shown in FIG. 10.

FIG. 11A is an exterior side view of two parts of a rotation cuff device useful for excluding the aneurysm of the vessel shown in FIG. 10. An outer cuff 290 has a polymeric compound (such as that used in conjunction with the inserts and apertures of the embodiment shown in FIGS. 2, 3 and 4) on various portion of the inner surface. Polymer coating is applied to at least one of the several areas shown. Generally there is continuous uninterrupted layer covering the coating area, though a striped coating configuration (as discussed above) can also be used. The coating area extends from the edge of the circular aperture (branch) or rectangular aperture outwardly from the opening and provides at least a minimum width contact area for the polymeric compound. While polymeric coatings are here shown on both pieces (outside of the inner one and on the inside of the outer one around both sets of openings), the polymeric coating can be configured with less initially coated area, such that the parts are configured to have a polymer coating in the space between layers around each branch related opening, when assembled. In this embodiment, edges of the polymer covered areas (coatings) on the inside surface are shown by dashed lines on the outer cuff 290 at opening 294. Opening 294 accommodates the inner cuff aperture 273. The insert cuff 270, having an insert aperture at 273 and the insert aperture 284 both have a polymeric compound area 280 disposed around their edge as shown by the cross hatched area. While rectangular shaped areas for the polymer are shown, other geometric shapes which provide an edge sealing zone or continuous seal completely around the opening can be used. Opening 284 accommodates the outer cuff aperture 293.

Figure 11B:
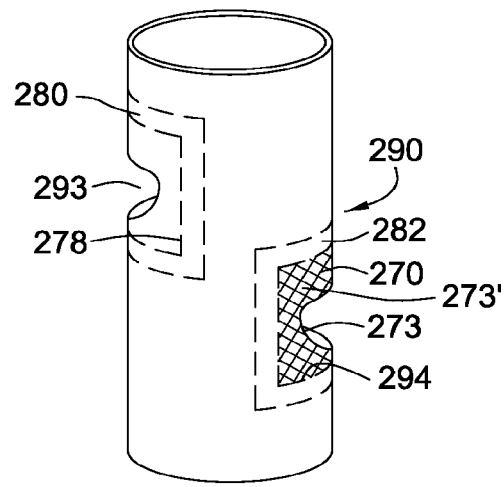
FIG. 11B is an exterior side view showing the two parts of the rotation cuff of FIG. 11A assembled with portions of each cuff shown in phantom.

FIG. 11B is an exterior side view showing the two parts 290, 270 of the rotation cuff of FIG. 11A assembled. A portion of the inner cuff 270 is seen through opening 294. The outer cuff aperture is seen at 293 and the inner cuff aperture is seen at 273. Areas having polymeric compound coatings are shown in dashed and cross hatched lines, 293' and 273' around outer cuff aperture 293 and inner cuff aperture 273.

Figure 11C:
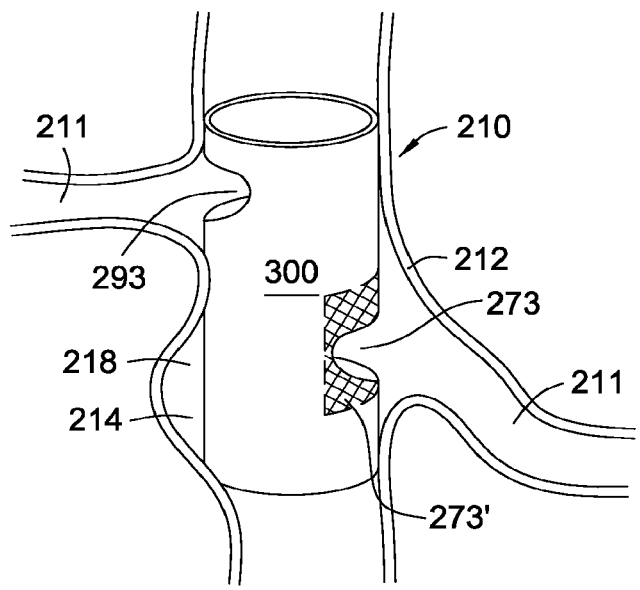
FIG. 11C is an exterior side view of the assembled cuff positioned in the branched region of the vessel shown in FIG. 10.

FIG. 11C is an exterior side of the assembled cuff of FIG. 11B positioned in the branched vessel region shown in FIG. 10. The aorta is seen at 210, the aortal wall is seen at 212, the aneurysmal region is shown at 214 and the aneurysmal sac is seen at 218. Branched arteries are seen at 216. The assembled cuff device is seen at 300, with outer cuff aperture 293 and inner cuff aperture 273 shown.

The stent grafts and cuffs according to the present invention may, optionally, deliver a therapeutic agent by way of a coating on the stent and/or graft material. In such an embodiment, the coating compound is adapted to exhibit a combination of physical characteristics such as biocompatibility, and, in some embodiments, biodegradability and bio-absorbability, while serving as a delivery vehicle for release of one or more therapeutic agents that aid in the treatment of aneurysmal or atherosclerotic tissue.

In selecting an appropriate therapeutic agent or agents, one objective is to protect the aneurysmal blood vessel from further destruction. Another objective is to promote healing. Generally, aneurysm results from the invasion of the cell wall by inflammatory agents that cause the release of elastin and collagen attacking proteins that for unknown reasons begin to congregate at certain blood vessel sites. Attack of the blood vessel structure causes further inflammation and cyclically the release of more of these elastin and collagen attacking proteins. Inflammation, the elastin and collagen attacking proteins, and the resulting breakdown of tissue, are leading causes of aneurysm formation.

Therapeutic agents useful in embodiments of the present invention include matrix metalloproteinase (MMP) inhibitors, which have been shown in some cases to reduce such elastin and collagen attacking proteins directly or in other cases indirectly by interfering with a precursor compound needed to synthesize the MMP's. Another class of agents, non-steroidal anti-inflammatory drugs (NSAIDs), has demonstrated anti-inflammatory qualities that reduce inflammation at the aneurysmal site, as well as an ability to block MMP-9 formation. Cyclooxygenase-2 or "COX-2" inhibitors also suppress MMP-9 formation. In addition, anti-adhesion molecules, such as anti-CD18 monoclonal antibody, limit the capability of leukocytes that may have taken up MMP-9 to attach to the blood vessel wall, thereby preventing MMP-9 from having the opportunity to attack the blood vessel extracellular matrix. Other therapeutic agents contemplated to be used to inhibit MMP-9 and possibly MMP-2 are tetracycline and related tetracycline-derivative compounds.

Steroidal anti-inflammatory drugs such as dexamethasone, beclomethasone and the like may be used to reduce inflammation. Another class of therapeutic agent that finds utility in inhibiting the progression of or inducing the regression of a pre-existing aneurysm is beta blockers or beta adrenergic blocking agents. In addition to therapeutic agents that inhibit elastases or reduce inflammation are agents that inhibit formation of angiotensin II, known as angiotensin converting enzyme (ACE) inhibitors. ACE inhibitors are known to alter vascular wall remodeling, and are used widely in the treatment of hypertension, congestive heart failure, and other cardiovascular disorders vascular wall injury.

The maximal dosage of the therapeutic to be administered is the highest dosage that effectively inhibits elastolytic, inflammatory or other aneurysmal activity, but does not cause undesirable or intolerable side effects. The dosage of the therapeutic agent or agents used will vary depending on properties of the stent, graft or coating material, including its time-release properties, whether the composition of the other components, and other properties. Also, the dosage of the therapeutic agent or agents used will vary depending on the potency, pathways of metabolism, extent of absorption, half-life and mechanisms of elimination of the therapeutic agent itself. In any event, the practitioner is guided by skill and knowledge in the field, and embodiments according to the present invention include without limitation dosages that are effective to achieve the described phenomena.

While the present invention has been described with reference to specific embodiments, it should be understood by those skilled in the art that various changes may be made and equivalents may be substituted without departing from the true spirit and scope of the invention. In addition, many modifications may be made to adapt a particular situation, material or process to the objective, spirit and scope of the present invention. All such modifications are intended to be within the scope of the invention.

All references cited herein are to aid in the understanding of the invention, and are incorporated in their entireties for all purposes.

What is claimed is:

1. A method of excluding a site of an aneurysm from blood flow comprising:
    delivering a stent graft in a compressed configuration to an abdominal aorta of a patient, the stent graft including a main body, wherein the main body includes a main body stent, a main body graft material coupled to the stent, and an aperture disposed through a surface of the main body graft material, wherein the aperture includes a neck portion extending outwardly from the main body, wherein the neck portion includes a neck portion graft material extending from and integral with the main body graft material and a neck portion stent;
    deploying the stent graft at the abdominal aorta by radially expanding the stent graft such that at least a portion of the main body is in apposition with a wall of the abdominal aorta and the neck portion is aligned with one of the renal arteries;
    delivering an insert in a compressed configuration such that an insertion end of the insert is disposed within the neck portion; and
    deploying the insert by radially expanding the insert such that the insertion end of the insert is disposed within the neck portion and a second portion of the insert extends from the neck portion and within one of the renal arteries,
    wherein at least one of the neck portion and the insert includes a polymeric compound different from the neck portion graft material and the insert graft material, wherein the polymeric compound is located on an inside surface of the neck portion graft material, an outside surface of an insertion end of the insert graft material, or on both the inside surface of the neck portion graft material and the outside surface of the insertion end of the insert graft material.

2. The method of claim 1, wherein delivering the insert comprises delivering the insert in the compressed configuration within a catheter through the stent graft main body and through the neck portion after the stent graft has been deployed.

3. The method of claim 1, wherein
    the stent graft comprises two apertures and two neck portions, wherein deploying the stent graft comprises aligning each of the two neck portions with a corresponding one of the renal arteries; and
    the insert comprises two inserts, wherein deploying the insert comprises deploying each insert into a corresponding one of the two neck portions.

4. The method of claim 3, wherein delivering the insert comprises delivering each of the two inserts in one catheter.

5. The method of claim 3, wherein delivering the insert comprises delivering each of the two inserts in a different catheter.

6. The method of claim 1, wherein the main body stent is made of shape memory material, and wherein the step of deploying the stent graft comprises retracting an outer sheath of a catheter to enable the shape memory material to self-expand.

7. The method of claim 1, wherein the stent graft is compressed over a balloon during the step of delivering the stent graft, and wherein deploying the stent graft comprises inflating the balloon.

8. The method of claim 1, wherein the main body stent comprises a plurality of wires, each of the wires bent into a zig-zag configuration and joined at opposing ends to form a hoop.

9. The method of claim 1, wherein the insert includes an insert stent and an insert graft material.

10. The method of claim 1, wherein
    the stent graft comprises four apertures and four neck portions, wherein deploying the stent graft comprises aligning each of the four neck portions with a corresponding one of the two renal arteries, the superior mesentery artery, and the celiac trunk; and
    the insert comprises four inserts, wherein deploying the insert comprises deploying each insert into a corresponding one of the four neck portions.

11. A method of excluding a site of an aneurysm from blood flow comprising:
    delivering a stent graft in a compressed configuration to an abdominal aorta of a patient, the stent graft including a main body, wherein the main body includes a main body stent, a main body graft material coupled to the stent, and an aperture disposed through a surface of the main body graft material, wherein the aperture includes a neck portion extending outwardly from the main body, wherein the neck portion includes a neck portion graft material extending from and integral with the main body graft material and a neck portion stent, wherein the main body includes an upstream portion and a downstream portion;

deploying the stent graft at the abdominal aorta by radially expanding the stent graft such that at least a portion of the main body is in apposition with a wall of the abdominal aorta and the neck portion is aligned with one of the renal arteries;

delivering an insert in a compressed configuration such that an insertion end of the insert is disposed within the neck portion;

deploying the insert by radially expanding the insert such that the insertion end of the insert is disposed within the neck portion and a second portion of the insert extends from the neck portion and within one of the renal arteries, delivering a second insert in a compressed configuration such that an upstream portion of the second insert is disposed within the downstream portion of the main body; and deploying the second insert by radially expanding the second insert such that the upstream portion of the second insert is disposed within the downstream portion of the main body and a second portion of the second insert extends downstream in the abdominal aorta.

12. The method of claim 11, wherein the second insert comprises a main portion, a first leg, and a second leg, wherein deploying delivering the second insert further comprises delivering the first leg to the right iliac artery.

13. The method of claim 12, further comprising delivering a third insert in a compressed configuration such that an insertion end of the third insert is disposed within the second leg of the second insert; and deploying the third insert by radially expanding the third insert such that the insertion end of the third insert is disposed within the second leg and a second portion of the third insert extends into the left iliac artery.

14. A method of excluding a site of an aneurysm from blood flow comprising:

delivering a stent graft in a compressed configuration to an abdominal aorta of a patient, the stent graft including a stent, graft material, an upstream portion, and a downstream portion;

deploying the stent graft at the abdominal aorta by radially expanding the stent graft such that at least a portion of the main body is in apposition with a wall of the abdominal aorta;

delivering an insert in a compressed configuration such that an upstream portion of the insert is disposed within the downstream portion of the stent graft, a first leg of the insert is disposed within the left iliac artery, and a second leg of the insert is disposed within the right iliac artery; and deploying the insert by radially expanding the insert such that upstream portion of the insert is disposed within the downstream portion of the stent graft, the first leg is in apposition with a wall of the left iliac artery, and the second leg is in apposition with a wall of the right iliac artery, the insert comprising an insert stent and insert graft material.

15. The method of claim 14, wherein at least one of the downstream portion of the stent graft and the upstream portion of the insert includes a polymeric compound different from the graft material and the insert graft material, wherein the polymeric compound is located on an inside surface of the graft material at the downstream portion of the stent graft, an outside surface of the upstream portion of the insert graft material, or on both the inside surface of the graft material at the downstream portion of the stent graft and the outside surface of the upstream portion of the insert graft material.

16. The method of claim 14, further comprising delivering a second insert in a compressed configuration such that an insertion end of the second insert is disposed within the first leg or the second leg of the insert; and deploying the second insert by radially expanding the second insert such that the insertion end of the second insert is disposed within the first leg or the second leg and a second portion of the second insert extends into the left iliac artery or the right iliac artery.

17. The method of claim 16, further comprising delivering a third insert in a compressed configuration such that an insertion end of the third insert is disposed within the first leg or the second leg of the insert that does not include the second insert; and deploying the third insert by radially expanding the second insert such that the insertion end of the third insert is disposed within the first leg or the second leg and a second portion of the third insert extends into the left iliac artery or the right iliac artery that does not include the second insert.

* * * * *